United States Patent
West et al.

(10) Patent No.: US 10,578,633 B2
(45) Date of Patent: Mar. 3, 2020

(54) METHODS AND DEVICES FOR ANALYSIS OF DEFINED MULTICELLULAR COMBINATIONS

(71) Applicant: Fluidigm Corporation, South San Francisco, CA (US)

(72) Inventors: Jason A. A. West, Pleasanton, CA (US); Brian Fowler, San Mateo, CA (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 0 days.

(21) Appl. No.: 14/775,685

(22) PCT Filed: Mar. 14, 2014

(86) PCT No.: PCT/US2014/029344
§ 371 (c)(1),
(2) Date: Sep. 12, 2015

(87) PCT Pub. No.: WO2014/144789
PCT Pub. Date: Sep. 18, 2014

(65) Prior Publication Data
US 2016/0025761 A1    Jan. 28, 2016

Related U.S. Application Data

(60) Provisional application No. 61/852,135, filed on Mar. 15, 2013.

(51) Int. Cl.
| | |
|---|---|
| *G01N 35/08* | (2006.01) |
| *G01N 33/50* | (2006.01) |
| *G01N 15/10* | (2006.01) |
| *G01N 15/14* | (2006.01) |
| *C12M 1/00* | (2006.01) |
| *G01N 33/569* | (2006.01) |
| *B01L 3/00* | (2006.01) |
| *C12M 1/04* | (2006.01) |

(52) U.S. Cl.
CPC ........ *G01N 35/08* (2013.01); *B01L 3/502738* (2013.01); *C12M 23/24* (2013.01); *C12M 29/04* (2013.01); *G01N 15/1056* (2013.01); *G01N 15/1484* (2013.01); *G01N 33/5005* (2013.01); *G01N 33/5097* (2013.01); *G01N 33/56961* (2013.01); *G01N 33/56966* (2013.01); *B01L 2200/027* (2013.01); *B01L 2200/0652* (2013.01); *B01L 2200/0668* (2013.01); *B01L 2200/10* (2013.01); *B01L 2300/0816* (2013.01); *B01L 2300/0864* (2013.01); *B01L 2300/0867* (2013.01); *B01L 2300/10* (2013.01); *B01L 2300/12* (2013.01); *B01L 2400/0487* (2013.01); *G01N 2015/1081* (2013.01)

(58) Field of Classification Search
None
See application file for complete search history.

(56) References Cited

U.S. PATENT DOCUMENTS

| | | | |
|---|---|---|---|
| 9,579,650 B2 | 2/2017 | Anderson et al. | |
| 2004/0229349 A1 | 11/2004 | Daridon | |
| 2011/0143949 A1* | 6/2011 | Heid | B01L 3/5027 506/7 |
| 2012/0100538 A1 | 4/2012 | Mikolajczyk et al. | |

FOREIGN PATENT DOCUMENTS

| | | |
|---|---|---|
| CN | 102414562 A | 4/2012 |
| EP | 2 381 116 A1 | 10/2011 |
| WO | 98/00231 A1 | 1/1998 |
| WO | 98/45481 A1 | 10/1998 |
| WO | 2004/025266 A2 | 3/2004 |
| WO | 2007/044091 A2 | 4/2007 |
| WO | 2007/044091 A3 | 4/2007 |
| WO | 200/9089189 A2 | 7/2009 |
| WO | 200/9089189 A3 | 7/2009 |
| WO | 2010/111388 A2 | 9/2010 |
| WO | 2012/162779 A1 | 12/2012 |
| WO | WO-2012178166 A1 * | 12/2012 ........... C12Q 1/6806 |

OTHER PUBLICATIONS

International Search Report and Written Opinion dated Oct. 22, 2014 for PCT Patent Application No. PCT/US2014/029344, 19 pages.
Wheeler et al., "Microfluidic Device for Single-Cell Analysis", Analytical Chemistry, vol. 75, No. 14, Jul. 15, 2003, pp. 3581-3586.
Xia et al., "A fully addressable micro-array chip integrated with cascade multiplexors for selective cell loading and retrieval", IEEE, Transducers, International Solid-State Sensors, Actuators and Microsystems Conference ; Denver, Jun. 2009, pp. 1301-1304.
EP14763560.1 , "Extended European search report", dated Oct. 5, 2016, 8 pages.

* cited by examiner

*Primary Examiner* — Emily A Cordas
(74) *Attorney, Agent, or Firm* — Kilpatrick Townsend & Stockton LLP

(57) ABSTRACT

Methods for cell analysis are provided, comprising cell capturing, characterization, transport, and culture. In an exemplary method individual cells (and/or cellular units) are flowed into a microfluidic channel, the channel is partitioned into a plurality of contiguous segments, capturing at least one cell in at least one segment, A characteristic of one or more captured cells is determined and the cell(s) and combinations of cells are transported to specified cell holding chamber(s) based on the determined characteristic(s). Also provided are devices and systems for cell analysis.

18 Claims, 18 Drawing Sheets

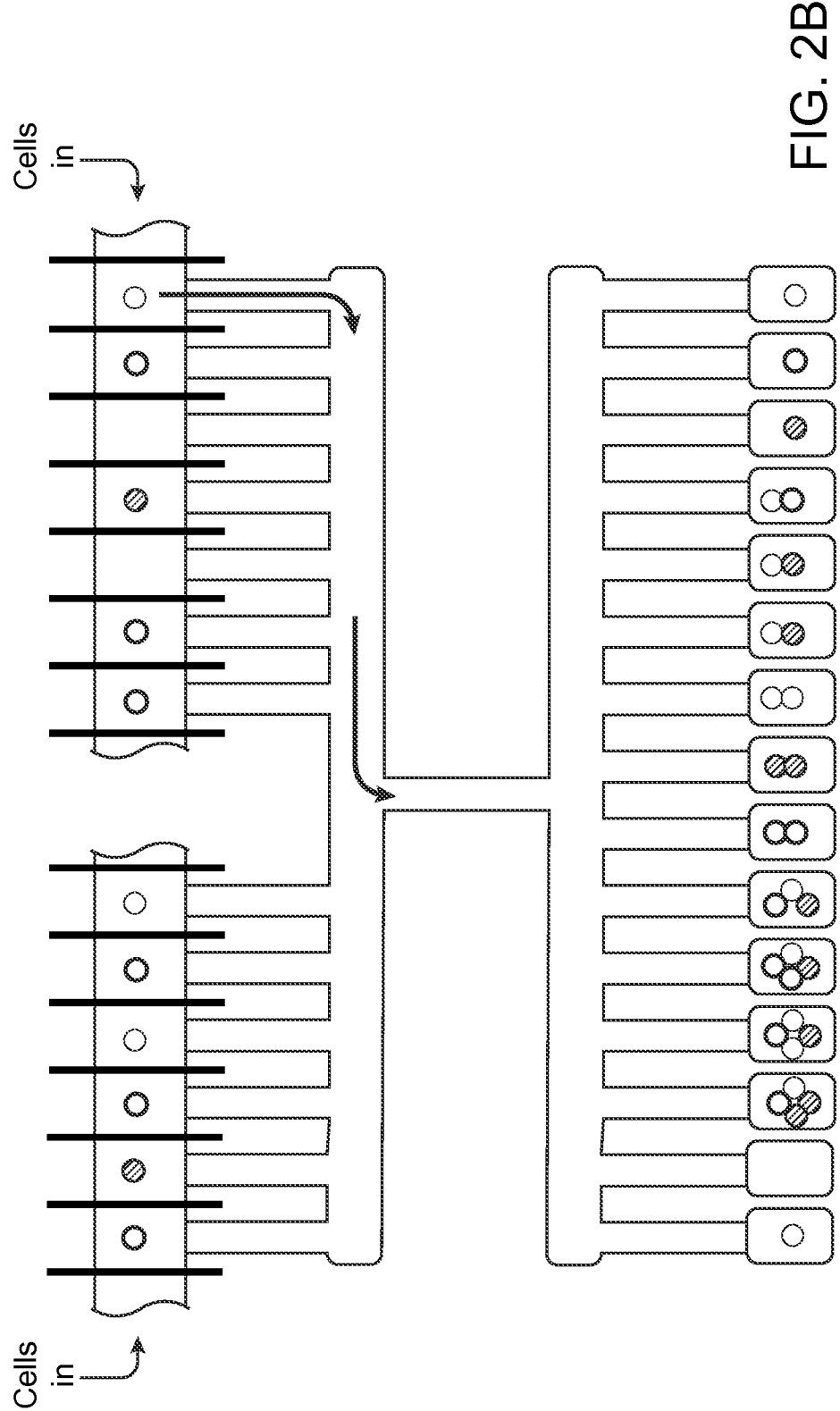

METHODS AND DEVICES FOR ANALYSIS OF DEFINED MULTICELLULAR COMBINATIONS

RELATED APPLICATIONS

This application is a US National Phase of PCT Application No. PCT/US2014/029344, filed on Mar. 14, 2014, which claims priority to U.S. provisional application No. 61/852,135 filed Mar. 13, 2013, the content of which is incorporated herein by reference.

FIELD OF THE INVENTION

The present invention relates to methods and devices for analysis of individual cells and defined combinations of cells.

BACKGROUND

A number of publications have discussed methods for manipulation of single cells, including the following (none of which is admitted to be prior art): Sims et al., 2007, "Analysis of single mammalian cells on-chip" Lab Chip 7:423-440; Wheeler et al., 2003, "Microfluidic device for single-cell analysis" Anal Chem 75:3581-3586; Skelley et al., 2009 "Microfluidic control of cell pairing and fusion" Nat Methods 6:147-152; Marcus et al., 2006, "Microfluidic single-cell mRNA isolation and analysis" Anal Chem 78:3084-3089; Bontoux et al., 2008 "Integrating whole transcriptome assays on a lab-on-a-chip for single cell gene profiling" Lab Chip 8:443-450; Zhong et al., 2008 "A microfluidic processor for gene expression profiling of single human embryonic stem cells" Lab Chip 8:68-74; Wheeler 2003 "Microfluidic Device for Single-Cell Analysis Anal. Chem." 75:3581-3586; and White et al., Aug. 23, 2011 "High-throughput microfluidic single-cell RT-qPCR PNAS" Vol. 108, 34:13999-14004. Each of the aforelisted publications is incorporated herein by reference.

The present invention provides a new method with features and advantages not found in prior art methods and devices.

BRIEF SUMMARY OF THE INVENTION

The present invention relates to methods and devices for analysis of individual cells and defined combinations of cells. The following embodiments are not intended to be limiting. Rather, it is understood that the examples and embodiments described herein are for illustrative purposes only and that various modifications or changes in light thereof will be suggested to persons skilled in the art and are to be included within the spirit and purview of this application In the following recitation of embodiments and throughout the entire specification, for simplicity, reference generally is made to an "individual cell" or a "single captured cell." For each and every such recitation, except where otherwise clear from context, it is contemplated that in alternative embodiments "individual cell" and a "single captured cell" should be read as "individual cellular unit" and "single captured cellular unit." Also contemplated are embodiments in which single cells are captured in some segments and process and single cell units are captured in other segments and processed.

In one aspect, the application discloses Aspect 1, which is a method for cell analysis, comprising carrying out at least two rounds of cell capturing, characterization, and transport, each round comprising: a) flowing a solution comprising a plurality of individual cells (and/or cellular units) into a first microfluidic channel; b) partitioning the channel into a plurality of contiguous segments (S), thereby capturing at least one cell in at least one segment, wherein i) one or more of said segments comprises a single captured cell (and/or single captured cellular unit), and c) determining at least one characteristic of one or more of said single captured cells and/or cellular units; and d) independently transporting each said captured cell or unit to a specified cell holding chamber based on the determined characteristic, whereby for each specified destination chamber the characteristic(s) of cell(s) transported thereto is known.

In one aspect, the application discloses Aspect 2, the method of aspect 1 wherein at least three, at least four, at least five, at least six, at least 10, at least 15, or at least 20 rounds of cell capturing, characterization, and transport are carried out.

In one aspect, the application discloses Aspect 3, the method of any preceding aspect wherein in (b) at least 30% of said segments comprise no more than one cell.

In one aspect, the application discloses Aspect 4, the method of aspect 3 wherein the majority of said segments comprise no more than one cell.

In one aspect, the application discloses Aspect 5, the method of any preceding aspect wherein one or more segments does not comprise any cell.

In one aspect, the application discloses Aspect 6, the method of any preceding aspect wherein the number of individual cells (or cellular units) flowed into the portion of the first microfluidic channel that is partitioned is less than the number of segments produced as a result of the partition.

In one aspect, the application discloses Aspect 7, the method of any preceding aspect wherein method is carried out in a device comprising two or more partitioning channels and a cell may be transported from any segment of any partitioning channel to any cell holding chamber.

In one aspect, the application discloses Aspect 8, the method of aspect 7 wherein there are two partitioning channels.

In one aspect, the application discloses Aspect 9, the method of any preceding aspect wherein the lumen of the first (partitioning) microfluidic channel is substantially featureless.

In one aspect, the application discloses Aspect 10, the method of any of aspects 1-9 wherein the characteristic determined is cell size, morphology, or the presence or absence of an extracellular or intracellular antigen.

In one aspect, the application discloses Aspect 11, the method of any of aspects 1-9 wherein the characteristic determined is a cell behavior.

In one aspect, the application discloses Aspect 12, the method of any of aspects 1-9 wherein the characteristic determined the response by the cell to a physical, chemical or biological challenge.

In one aspect, the application discloses Aspect 13, the method of any preceding aspect wherein said cells are transported by bulk fluid flow.

In one aspect, the application discloses Aspect 14, the method of any preceding aspect wherein a compound manifold system is used to transport cells from any segment to any cell holding chamber.

In one aspect, the application discloses Aspect 15, the method of any preceding aspect wherein each cell transported from a segment to a cell holding chamber is transported though (e.g., flows though) the same connector channel.

In one aspect, the application discloses Aspect 16, the method of any preceding aspect wherein each of said segments is in fluidic communication with a common second microfluidic channel, and said captured cells are transported through the second microfluidic channel in transit to a specified cell holding chamber.

In one aspect, the application discloses Aspect 17, the method of any preceding aspect in which at least 10 individual cells (or cellular units) are transported from segments to cell holding chambers and/or at least 10 cell holding chambers are occupied by cells.

In one aspect, the application discloses Aspect 18, the method of aspect 16 or 17 in which the compound manifold connects at least 5 segments and at least 5 cell holding chambers.

In one aspect, the application discloses Aspect 19, the method of aspect 18 in which the compound manifold connects at least 10 segments and at least 10 cell holding chambers.

In one aspect, the application discloses Aspect 20, the method of aspect 19 in which the compound manifold connects at least 10 segments and at least 10 cell holding chambers.

In one aspect, the application discloses Aspect 21, the method of aspect 20 in which the compound manifold connects at least 20 segments and at least 20 cell holding chambers.

In one aspect, the application discloses Aspect 22, the method of aspect 21 in which the compound manifold connects at least 10 segments and at least 10 to 100 cell holding chambers.

In one aspect, the application discloses Aspect 23, the method of aspect 22 in which the compound manifold connects at least 50 segments and at least 50-100 cell holding chambers.

In one aspect, the application discloses Aspect 24, the method of any preceding aspect wherein the ratio of the number of segments to the number of cell holding chambers is greater than 1.

In one aspect, the application discloses Aspect 25, the method of aspect 24 wherein the number of segments is greater than the number of cell holding chambers by a factor of about 10%, about 20%, about 50% about 75% about 100% or about 200%.

In one aspect, the application discloses Aspect 26, the method of any preceding aspect in which multiple cells are individually transported to the same cell holding chamber, thereby producing a cell holding chamber comprising a defined combination of cells.

In one aspect, the application discloses Aspect 27, the method of aspect 26 in which two, three or four cells are individually transported to the same cell holding chamber.

In one aspect, the application discloses Aspect 28, the method of aspect 27 in which each individually transported cell is captured in a different round of partitioning.

In one aspect, the application discloses Aspect 29, the method of any preceding aspect wherein the cells flowed into the first microfluidic channel are eukaryotic cells.

In one aspect, the application discloses Aspect 30, the method of aspect 29 wherein the cells are animal cells.

In one aspect, the application discloses Aspect 31, the method of aspect 30 wherein the cells are human.

In one aspect, the application discloses Aspect 32, the method of any preceding aspect wherein the cells are plant cells.

In one aspect, the application discloses Aspect 33, the method of any preceding aspect wherein the solution comprising a plurality of individual cells (or cellular units) in (a) comprises cells from two different eukaryotic species.

In one aspect, the application discloses Aspect 34, the method of any preceding aspect wherein the solution comprising a plurality of individual cells (or cellular units) in (a) comprises cells from two different individuals or specimens of the same species.

In one aspect, the application discloses Aspect 35, the method of any preceding aspect, wherein the plurality of individual cells (or cellular units) in (a) comprises rare cells and other cells, at least one cell that is transported in step (d) to a cell holding chamber is a rare cell, and the ratio in said solution of said other cells to said rare cells is greater than 100:1, sometimes greater than 1000:1, sometimes greater than 10,000:1, and sometimes greater than 100,000:1.

In one aspect, the application discloses Aspect 36, the method of aspect 35 wherein the rare cell is a stem cell, a tumor cell, optionally a circulating tumor cell, a circulating endothelial cell, or a fetal cell.

In one aspect, the application discloses Aspect 37, the method of any of aspects 1-36 in which cells are cultured in the cell holding chamber.

In one aspect, the application discloses Aspect 38, the method of aspect 37 in which the cells are cultured for from about 1 hour to about 4 weeks.

In one aspect, the application discloses Aspect 39, the method of aspect 37 in which the cells are cultured for from about 1 hour to about 24 hours.

In one aspect, the application discloses Aspect 40, the method of any of aspects 37-39 in which the cells divide to produce progeny.

In one aspect, the application discloses Aspect 41, the method of any of aspects 37-40 in which the cells are observed during culture.

In one aspect, the application discloses Aspect 42, the method of any of aspects 37-41 in which the cells are challenged during culture.

In one aspect, the application discloses Aspect 43, the method of any of aspects 37-42 in which the challenge comprises exposing the cells to an agent In one aspect, the application discloses Aspect 44, the method of aspect 43 in which the agent is a drug, test agent, protein, nucleic acid or small molecule.

In one aspect, the application discloses Aspect 45, the method of any of aspects 37-44 in which a first cell or combination of cells is cultured for at least one hour, and then one or more additional cells obtained by cell capturing, characterization, and transport in the device is introduced into the cell holding chamber.

In one aspect, the application discloses Aspect 46, the method of any of aspects 37-45 wherein after a period of culture, viable cells are harvested from a cell holding chamber.

In one aspect, the application discloses Aspect 47, the method of any of aspects 37-46 wherein after a period of culture, cells in a cell holding chamber are fixed in situ.

In one aspect, the application discloses Aspect 48, the method of any of aspects 37-45 in which a reagent, solution or physical stimulus is applied to a cell or cells in one or more cell holding chambers, and results in lysis of said cell or cells.

In one aspect, the application discloses Aspect 49, the method of aspect 48 wherein macromolecules released from the lysed cells are transported out of at least one cell holding chamber.

In one aspect, the application discloses Aspect 50, the method of aspect 49 wherein macromolecules are collected.

In one aspect, the application discloses Aspect 51, the method of aspect 49 wherein macromolecules released from the lysed cells are transported out of a the cell holding chamber into a corresponding microfluidic chamber, wherein the corresponding microfluidic chamber is in fluidic communication with said cell holding chamber and not with other cell holding chambers.

In one aspect, the application discloses Aspect 52, the method of aspect 50 or 51 wherein the macromolecules are nucleic acids, optionally the nucleic acids are amplified (optionally reverse transcribed), and optionally the nucleic acids or corresponding amplicons are assayed in the microfluidic system wherein said steps occur all occur within the fluidic circuit, where optionally the assay determined a genetic characteristic or gene, RNA or protein expression pattern.

In one aspect, the application discloses Aspect 53, a chamber in a microfluidic device that is configured for receiving and maintaining live cells, the chamber comprising: an input channel configured so that nucleated eukaryotic cells can pass intact through the input channel and into the chamber; a plurality of four or more drain channels configured so that fluid but not nucleated eukaryotic cells can exit the chamber; and a gas permeable membrane separating the chamber from a supply channel, wherein the supply channel is configured to bring a gaseous mixture to the chamber, and the gas permeable membrane is configured so that gasses may be exchanged between the chamber and the supply channel.

In one aspect, the application discloses Aspect 54, the chamber of aspect 53, wherein the chamber or the input channel is connected to a reagent channel configured for supplying a fluid comprising one or more reagents for maintaining or treating cells in the chamber.

In one aspect, the application discloses Aspect 55, the chamber of aspect 54, wherein the reagent channel is connected to a supply of a fluid containing cell nutrients.

In one aspect, the application discloses Aspect 56, the chamber of aspect 54, wherein the reagent channel is connected to a supply of a fluid that lyses cells upon delivery of the fluid into the chamber.

In one aspect, the application discloses Aspect 57, the chamber of any of aspects 53-56, wherein the input channel tapers towards the chamber, thereby directing cells towards the chamber's center.

In one aspect, the application discloses Aspect 58, the chamber of any of aspects 53-57, wherein the drain channels are distributed around the chamber in a manner that allows fluid to flow from the input channel into the chamber and out the drain channels without drawing cells in the chamber towards the drain channels.

In one aspect, the application discloses Aspect 59, the chamber of aspect 58, wherein the chamber has a perimeter that is substantially circular or oval in shape, and the drain channels are distributed over more than 180 degrees of the perimeter.

In one aspect, the application discloses Aspect 60, the chamber of any of aspects 53-59, comprising ten or more drain channels.

In one aspect, the application discloses Aspect 61, chamber of any of aspects 53-60, wherein the drain channels connect to the chamber through drain openings and the input channel connects to the channel though an input opening, and the diameter of the drain openings is less than 20% of the diameter of the input opening, thereby inhibiting passage of intact cells into the drain channels.

In one aspect, the application discloses Aspect 62, the chamber of any of aspects 53-61, wherein the drain channels contain beads or a filter, thereby inhibiting passage of intact cells into the drain channels.

In one aspect, the application discloses Aspect 63, the chamber of any of aspects 53-62, large enough to accommodate at least 3 eukaryotic cells.

In one aspect, the application discloses Aspect 64, the chamber of any of aspects 53-63, large enough to accommodate at least 10 eukaryotic cells.

In one aspect, the application discloses Aspect 65, the chamber of any of aspects 53-64, at least 50 microns across at its narrowest diameter.

In one aspect, the application discloses Aspect 66, the chamber of any of aspects 53-65, at least 200 microns across at its narrowest diameter.

In one aspect, the application discloses Aspect 67, the chamber of any of aspects 53-66, comprising a convex lower surface.

In one aspect, the application discloses Aspect 68, the chamber of any of aspects 53-67, comprising a lower surface coated with a substance that promotes cell adhesion.

In one aspect, the application discloses Aspect 69, the chamber of aspect 68, wherein the substance is an extracellular matrix.

In one aspect, the application discloses Aspect 70, the chamber of aspect 68, wherein the substance is fibronectin.

In one aspect, the application discloses Aspect 71, the chamber of any of aspects 53-70, wherein the chamber, the input channel, and the drain channels are filled with fluid.

In one aspect, the application discloses Aspect 72, the chamber of any of aspects 53-71, containing at least two eukaryotic cells.

In one aspect, the application discloses Aspect 73, a device comprising a plurality of four or more chambers according to any of aspects 53-71, each having its own separate input channel, wherein each of the input channels is configured to supply cells from a common source.

In one aspect, the application discloses Aspect 74, a device according to aspect 73, wherein the separate input channels each has a valve that can be operated independently of valves in the other input channels.

In one aspect, the application discloses Aspect 75, a device according to aspect 73 or 74, wherein the separate input channels are part of a first multiplexer, and the common source is a connection channel that connects the first multiplexer to a second multiplexer, wherein the second multiplexer is configured to deliver cells from a plurality of different sources to the connection channel.

In one aspect, the application discloses Aspect 76, a device according to aspect 75, wherein the different sources are partitioned regions of a common partitioning channel.

In one aspect, the application discloses Aspect 77, a method of maintaining cells in culture, comprising delivering cells to a chamber according to any of aspects 53-72, supplying nutrient medium into the chamber through the input channel or a separate reagent channel, and supplying gas to the gas permeable membrane through the supply channel.

In one aspect, the application discloses Aspect 78, the method of aspect 77, further comprising individually selecting the cells delivered to the chamber from a cell mixture.

In one aspect, the application discloses Aspect 79, the method of extracting intracellular components from one or more cells that are present in a chamber according to any of aspects 53-72, comprising lysing the cells by delivering a fluid that causes cell lysis into the chamber, and retrieving products of the lysis from the chamber.

In one aspect, the application discloses Aspect 80, the method of aspect 79, wherein the products are retrieved through the drain channels.

In one aspect, the application discloses Aspect 81, the method of aspect 79 or 80, wherein the products comprise nucleic acid.

In one aspect, the application discloses Aspect 82, the method of any of aspects 78-81, further comprising subjecting the products to a chemical or biochemical reaction.

In one aspect, the application discloses Aspect 83, an arrangement of channels and valves in a microfluidic device, comprising: (a) an input multiplexer that comprises: (i) a plurality of four or more input channels; (ii) a plurality of input valves configured and arranged to control the input channels such that fluid in any one of the input channels may flow independently of fluid in the other input channels; (iii) one or more combining channels configured and arranged to receive fluid flowing through any one or more of the input channels and to send the fluid through a single connecting channel; (b) the connecting channel; and (c) an output multiplexer that comprises: (i) a plurality of four or more output channels; (ii) a plurality of output valves configured and arranged to control the output channels such that fluid in any one of the output channels may flow independently of fluid in the other output channels; (iii) one or more distributing channels configured and arranged to receive fluid flowing through the connecting channel and to send the fluid through any one or more of the output channels depending on operation of the output valves.

In one aspect, the application discloses Aspect 84, the arrangement of aspect 83, wherein the one or more combining channels is a manifold.

In one aspect, the application discloses Aspect 85, the arrangement of aspect 83 or 84, wherein the path length from any one of the input channels through the combining channels to the connecting channel is the same.

In one aspect, the application discloses Aspect 86, the arrangement of any of aspects 83-85, wherein the one or more distributing channels is a manifold.

In one aspect, the application discloses Aspect 87, the arrangement of any of aspects 83-86, wherein the path length from the connecting channel through the distributing channels to any one of the output channels is the same.

In one aspect, the application discloses Aspect 88, the arrangement of any of aspects 83 to 87, configured so that a eukaryotic cell may pass intact through and from any one of the input channels, through the combining channels, through the connection channel, through the distributing channels, and through any one of the output channels.

In one aspect, the application discloses Aspect 89, the arrangement of any of aspects 83-88, wherein each of the input channels connects to and is configured to receive fluid from a different region of a partitioning channel.

In one aspect, the application discloses Aspect 90, the arrangement of aspect 89, wherein the input valves are positioned between the partitioning channel and the combining channels.

In one aspect, the application discloses Aspect 91, the arrangement of aspect 89, wherein the partitioning channel is positioned between the input valves and the partitioning channel.

In one aspect, the application discloses Aspect 92, the arrangement of any of aspects 83-91, wherein a plurality of the output channels each connects to a separate holding chamber.

In one aspect, the application discloses Aspect 93, the arrangement of aspect 92, wherein the holding chamber is configured for cell culture.

In one aspect, the application discloses Aspect 94, the arrangement of any of aspects 91-93, wherein the channels in the input manifold, the connecting channel, and the channels in the output manifold are all filled with fluid.

In one aspect, the application discloses Aspect 95, an apparatus configured to support and operate a microfluidic device, comprising: (a) a platform that comprises: (i) a cavity shaped and sized to receive and support a microfluidic device; (ii) optically transparent (e.g., glass) window positioned above the cavity so that when cells are being processed by a device in the cavity, the cells may be imaged through the window; (iii) an interface plate that comprises a plurality of openings configured to seal to control channels in a microfluidic device in the cavity and to operate valves in the device by pneumatic pressure; (iv) an integral heating member that surrounds the cavity in the plane of the platform, configured to maintain a microfluidic device in the cavity at a temperature suitable for cell culture; (b) a mix box that comprises: (i) an inlet configured to receive a gas mixture; (ii) a humidifier configured to humidify the gas mixture; (iii) a heater configured to heat the gas mixture to a temperature suitable for cell culture; and (c) a conduit configured so that gas heated by the heater in the mix box may pass through the platform into a microfluidic device in the cavity.

In one aspect, the application discloses Aspect 96, the apparatus of aspect 95, further comprising: (d) a conduit configured so that spent gas from a microfluidic device in the cavity may pass back to and out through the mix box; and (e) a conduit configured so that spent liquid from a microfluidic device in the cavity may pass back to and out through the mix box.

In one aspect, the application discloses Aspect 97, the apparatus of aspect 95 or 96, wherein the platform further comprises: (v) a humidity sensor configured to determine humidity of a gas mixture passing into and/or out of a microfluidic device in the cavity.

In one aspect, the application discloses Aspect 98, the apparatus of aspects 95-97, wherein the mix box further comprises: (iv) a luer lock connecter configured to connect the inlet to a source of gas mixture; and (v) an electrical socket.

In one aspect, the application discloses Aspect 99, the apparatus of any of aspects 95-98, wherein the integral heating member passes from the platform to the mix box so as to heat a microfluidic device in the cavity and a gas mixture in the mix box at the same time.

In one aspect, the application discloses Aspect 100, the apparatus of any of aspects 95-99, wherein the integral heating member comprises polyamide.

In one aspect, the application discloses Aspect 101, the apparatus of any of aspects 95-100, wherein the optically transparent (e.g., glass) window is coated with a coating that inhibits condensation.

In one aspect, the application discloses Aspect 102, the apparatus of aspect 101, wherein the coating comprises iridium and tin.

In one aspect, the application discloses Aspect 103, a microfluidic system comprising a support apparatus according to any of aspects 95-98 with a microfluidic device in the cavity.

In one aspect, the application discloses Aspect 104, the microfluidic system of aspect 103, wherein the microfluidic device is a device as hereinbefore described.

In one aspect, the application discloses Aspect 105, the microfluidic system of aspect 103 or 104, further comprising a supply of a gas mixture and a supply of nutrient medium for culturing cells in the microfluidic device.

In one aspect, the application discloses Aspect 106, the microfluidic system of any of aspects 103-105, further comprising an imaging apparatus configured to capture images of cells in the microfluidic device.

In one aspect, the application discloses Aspect 107, the microfluidic system of any of aspects 103-106, further comprising a computer processor configured and programmed to control operation of the microfluidic device.

In one aspect, the application discloses Aspect 108, the microfluidic system of aspect 107, wherein the computer processor is a dedicated processor.

In one aspect, the application discloses Aspect 109, the microfluidic system of aspect 107, wherein the computer processor is a processor in a portable computer system comprising an app coded to control operation of the microfluidic device.

In one aspect, the application discloses Aspect 110, the microfluidic system of aspects 107 to 109, wherein the computer processor is configured and programmed to display images of cells in the microfluidic device.

In one aspect, the application discloses Aspect 111, use of a partitioning channel in a microfluidic device as heretofore described in the processing of a cell population.

In one aspect, the application discloses Aspect 112, use of an input multiplexer connected to an output multiplexer in a microfluidic device as heretofore described in the processing of a cell population.

In one aspect, the application discloses Aspect 113, use of a plurality of holding chambers in a microfluidic device as heretofore described in the processing of a cell population.

In one aspect, the application discloses Aspect 114, use of a support apparatus for a microfluidic device as heretofore described in the processing of a cell population.

In one aspect, the application discloses Aspect 115, use according to any of aspects 111-114, wherein the processing comprises separating and sorting individual cells (or cellular units) from the cell population.

In one aspect, the application discloses Aspect 116, use according to any of aspects 111-115, wherein the processing comprises separately culturing individual cells (or cellular units) from the cell population.

In one aspect, the application discloses Aspect 117, use according to any of aspects 111-116, wherein the processing comprises separating and combining individual cells (or cellular units) from the cell population with other individual cells (or cellular units) separated from the cell population.

In one aspect, the application discloses Aspect 118, use according to any of aspects 111-117, wherein the processing comprises separately collecting contents of individual cells (or cellular units) from the population and subjecting the contents of each cell to a chemical reaction.

In one aspect, the application discloses Aspect 119, use according to aspect 118, wherein the chemical reaction is part of an assay.

In one aspect, the application discloses Aspect 120, use according to any of aspects 118-119, wherein the processing comprises separately imaging individual cells (or cellular units) from the population.

In one aspect, the application discloses Aspect 121, a method of determining properties of a population of cells comprising providing an acellular composition comprising macromolecules from exactly N cells, where N=2, wherein said N cells have been cultured together for at least 2 hours, and carrying out an analytical step on said macromolecules.

In one aspect, the application discloses Aspect 122, the method of aspect 121 wherein the macromolecules are nucleic acids and the analytical step comprises amplification, transcription, reverse transcription, cloning or sequencing.

In one aspect, the application discloses Aspect 123, the method of aspect 121 wherein the macromolecules are proteins and the analytical step comprises combining the proteins with an antibody.

In one aspect, the application discloses Aspect 124, the method of any of aspects 121-123 except N=3, 4, 5, 6, 7, 8 or is less than 10.

BRIEF DESCRIPTION OF THE DRAWINGS

FIGS. 2A and 2B shows schematic of embodiment of the invention including a partitioning channel(s) and valves spaced along a length of the channel(s). The multiplexor is not shown. FIG. 2A shows an embodiment with one partitioning channel and FIG. 2B shows an embodiment with two partitioning channels.

FIGS. 3A and 3B illustrate two positional relationships of the partitioning channel and multiplexors.

FIG. 4 shows an exemplary design of a device.

DETAILED DESCRIPTION OF THE INVENTION

1. Introduction

The present invention relates to methods and devices for analysis of individual cells (or cellular units) and defined combinations of cells. The method includes using a microfluidic system for carrying out several rounds of cell capturing, characterization, and transport. Cells and combinations of cells are cultured together and may be subject to further analysis or manipulation including genotyping, nucleic acid amplification and preamplification, analysis of gene expression, treatment with miRNA, analysis (e.g., activity assays) of DNA and protein targets.

Figure 1:
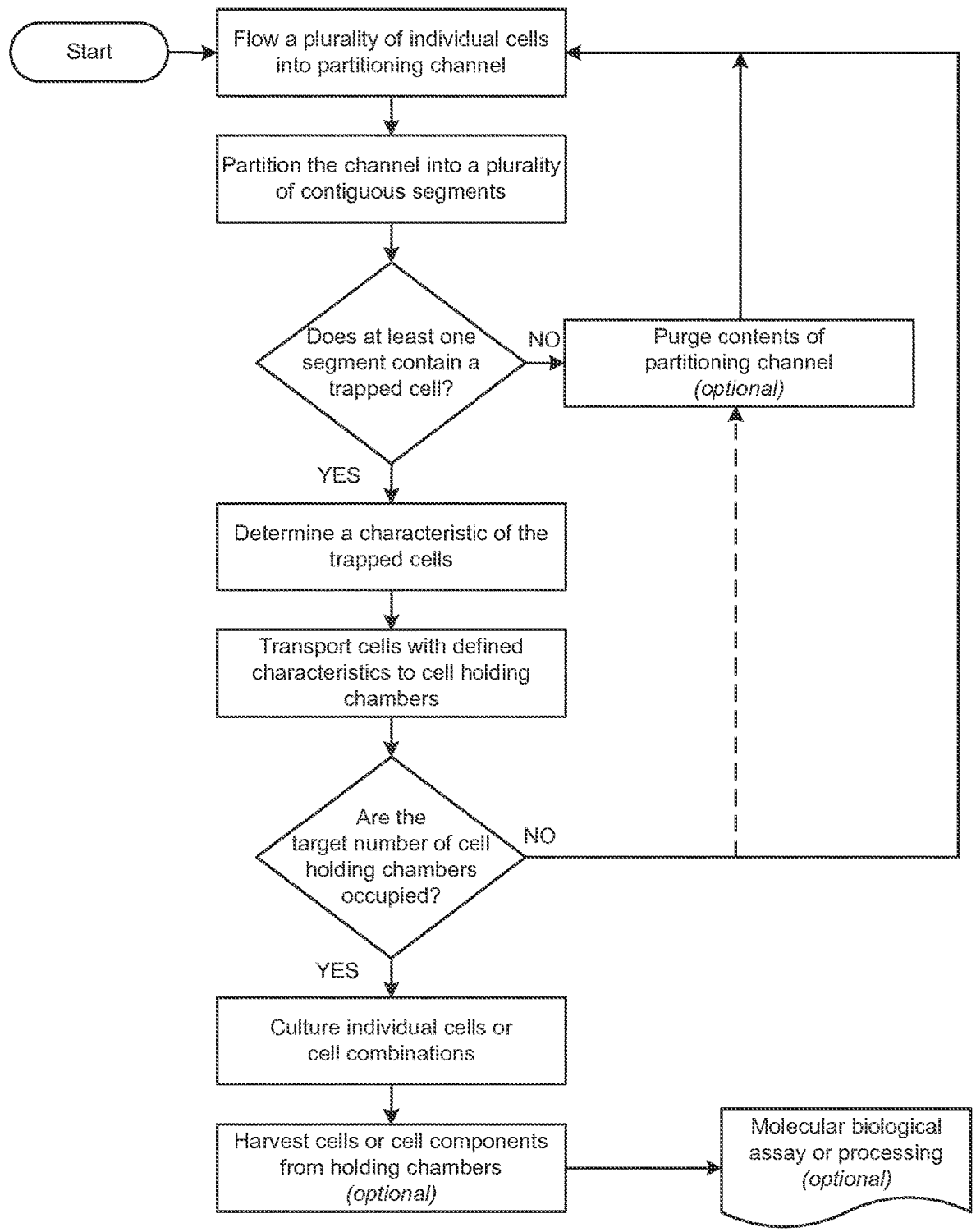
FIG. 1 is a flow chart showing exemplary steps for carrying out the invention.

In one aspect, the invention provides a method for cell analysis by comprising carrying out at least two rounds of cell capturing, characterization, and transport, each round comprising a) flowing a solution comprising a plurality of individual cells (or cellular units) into a first microfluidic channel; b) partitioning the channel into a plurality of contiguous segments, thereby capturing at least one cell in at least one segment, wherein one or more of said segments comprises a single captured cell or single captured cell unit; c) determining at least one characteristic of one or more of said single captured cells or single captured cell units; and d) independently transporting each said captured cell or single captured cell unit to a specified destination chamber based on the determined characteristic, whereby for each specified destination chamber the characteristic(s) of cell(s) transported thereto is known. Cells and combinations of cells are analyzed directly, cultured and, optionally, harvested for molecular biological processing. See FIG. 1.

A variety of methods and devices for cell isolation and manipulation are disclosed in U.S. patent application Ser. No. 13/781,292, filed Feb. 28, 2013 and published as US 2013-0302883 A1, which is incorporated herein in its entirety all purposes.

2. Definitions

"Plurality" means at least three.

"Majority" means more than 50%.

A "cell" may be a eukaryotic cell or a prokaryotic cell.

An "individual cell" is a cell that is not in physical contact with other cells, e.g., is not part of a solid tissue or multicellular structure. An individual cell may be one that in its naturally state is, at least for a portion of its life, not in contact with other cells (e.g., circulating lymphocytes; spermatozoa, oocytes, nucleated red blood cells, single cell algae, protozoa and the like). Alternatively, an individual cell may be one that in its naturally state is generally in contact with other cells (e.g., hepatocytes, neurons) but which has been separated from those other cells (e.g., by disaggregation of a tissue).

An "individual cellular unit" is an aggregation of a small number of cells (e.g., 2, 3, 4, 5 cells, or less than 10 cells and/or aggregation of a small number of cells having a size capable of flowing through a microfluidic channel with a 1000 micron diameter lumen). For illustration, a pluripotent stem cell aggregate may be a cellular unit.

The phrase "individual cells (or cellular units)" should be read as "In some embodiments, individual cells; In other embodiments individual cellular units" and "In still other embodiments a mixture of individual cells and cellular units. Likewise, the phrase "single captured cells or single captured cell units" should be read as "In some embodiments, single captured cells; In other embodiments single captured individual cellular units" and "In still other embodiments a mixture of single captured cells and single captured cellular units."

Two components of a microfluidic device are referred to as "fluidically connected" when they are connected by a microfluidic channel or other conduit that can carry fluid from one of the components to the other.

"Valves" are used to restrict movement of cells and/or movement of fluid (air or liquid) through a channel. As discussed herein below (§ 17A), valves may have a variety of designs and structures. In addition, valves may be referred to by function (e.g., "partition valves," "upstream valves," downstream valves, "multiplexor valves," "permeable valves," "one way valves," and "pump valves").

A "channel filter" refers to a non-actuatable barrier in a channel (e.g., an upstream channel or a drain channel) that prevents passage of cells through or into the channel but allows liquid to flow through. In some embodiments the filter is made by packing a portion of the channel with beads or comprises frits, posts, porous polymer monolithic materials, and the like.

A "length" of a microfluidic channel refers to a channel or portion of a channel into which cells are introduced and which is partitioned into a plurality of contiguous segments.

"Capturing" refers to using a physical barrier to confine a cell to a particular segment of a channel As used herein, "address" refers to a location in a microfluidic system. For example, in a microfluidic system of the invention each segment may be assigned an address (e.g., 1-10) and each cell holding chamber may be assigned an address (e.g., a-z).

3. Partitioning Channel

Figure 2A:
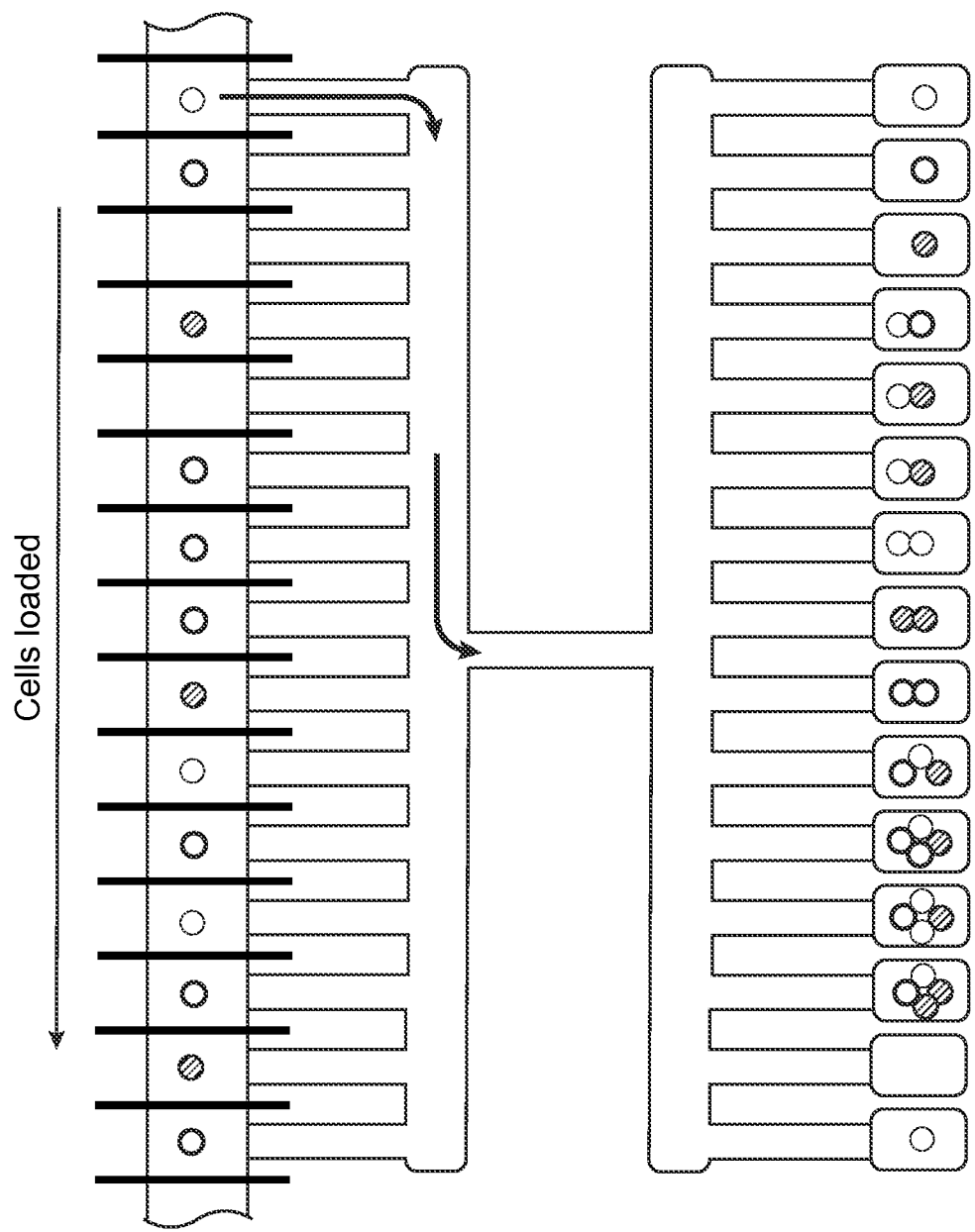

Individual cells (or cellular units) may be isolated by flowing a composition comprising a plurality of cells into a microfluidic channel (referred to as a "partitioning channel") and physically isolating at least one individual cell from other cells in the channel. The step of physically isolating may be accomplished by partitioning the partitioning channel into a plurality of segments, at least one of which contains a single cell. FIG. 2A illustrates a partitioning channel and valves spaced along a length of the channel. When the valves are actuated, the channel is partitioned into a plurality of segments. (In FIG. 2A and certain other schematic figures, the positions of the selected values are illustrated using elongated solid rectangles. It will be apparent from context which valves are open or closed during a particular operation. Not all valves are shown.)

The dimensions of the partitioning channel may vary depending on the channel materials, valve design, and other factors, but in any event dimensions are sufficient to allow a cell, generally a eukaryotic cell, to flow through the channel. Dimensions of eukaryotic cells are generally in the range of about 4 to about 100 microns. Exemplary cross-sectional dimensions for partitioning channels are about 15 microns to about 1000 microns, about 15 microns to about 500 microns, sometimes about 500 microns to about 1000 microns, sometimes about 200 microns to about 800 microns.

It will be understood and clear from context that reference to "partitioning channel" often refers to the portion of the partitioning channel along which valves are actuated to make segments. It will be understood that the partitioning channel will usually have segments that lack partition valves, typically at both ends, through which cells are introduced or withdrawn from the channel. In some embodiments, the microfluidic system comprises multiple (e.g., two) partitioning channels. See § 4, below.

4. Introducing Cells into the Partitioning Channel

In a first step in the process of the invention, a solution containing cells is flowed into the partitioning channel, and into the length of the channel in which cells are captured.

Generally the cells are in a solution in which the cells are viable, such as a cell culture medium.

It is within the ability of a person of ordinary skill in the art to identify an appropriate medium for cells being studied. In some embodiments the cells are maintained at a specified temperature (e.g., room temperature or 37 degrees C.), humidity, and/or atmosphere (e.g., $CO_2/O_2$ partial pressure).

Prior to introducing cells into the partitioning channel they may be stored in a reservoir that is permanently or reversibly in fluid communication with the partitioning channel.

Cells are generally introduced into the partitioning channel by bulk fluid flow, as described in § 9 below but may be introduced into the partitioning channel using other methods of transport, as known in the art and also described in § 9 below.

In some embodiments, the microfluidic system comprises multiple (e.g., 2) partitioning channels. See FIG. 2B. A device with multiple partitioning channels may have advantages when two distinctly different cell populations or types are being analyzed and combined, especially cells that are of significantly different sizes, cells for which different characteristics are being determined, cells that require different media, experiments in which cross-contamination between cell preparations must be avoided, and the like.

Alternatively, as discussed below, different cells populations or types can be introduced into the same partitioning channel at different times (e.g. sequentially). Alternatively, different cell types, or different cell populations can be mixed and selected after capture based on determined characteristics. Frequently, a sample is obtained that contains a mixture of different cell types and the methods and systems of the invention are used to select individual cells (or cellular units) of interest from the mixture, usually discarding the other cells.

In some embodiments the cells of interest are rare in the population. For example, the in the solution introduced into the partitioning chamber the ratio of cells of interest to other cells may be greater than 100:1, sometimes greater than 1000:1, sometimes greater than 10,000:1, and sometimes greater than 100,000:1. Examples of rare cells include stem cells, tumor cells (e.g., a circulating tumor cell), circulating endothelial cells, and fetal cells.

5. Valves, Partitioning, Segments

As noted above, valves are spaced along a length of the partitioning channel, which valves may be actuated to partition the channel into a plurality of segments.

As used herein, the term "valves" refers to structures used to restrict movement of cells and/or movement of liquid through a channel. Valves are actuatable (can be closed or opened in response to an actuation signal) and generally reversible (can both be closed and opened in response to a signal or signals). As discussed herein below in § 17A, valves may have a variety of designs and structures. In addition, valves may be referred to by function (e.g., "partition valves," "upstream valves," downstream valves, "multiplexor valves," "permeable valves," "one way valves," and "pump valves").

Some valves stop movement of liquid through a channel (e.g., by completely blocking the channel lumen). These valves will also block movement of cells though the channel. "Permeable" valves block cell movement but allow liquid to flow through them. For example, a partially closed valve can block enough of the lumen to prevent cell passage while letting fluid through. One approach to partially closed valves is found in, e.g., US Pat. Pub. 20080264863 to Quake (describing sieve valves). Another permeable valve is a valve having pillars integral to the membrane structure, so that when the valves are closed the pillars maintain gaps that allow fluid, but not cells, to flow through. See, e.g., FIG. 27AB of U.S. Pat. No. 7,291,512. Nonactuatable channel "filters" are described below, and also allow block cell movement but allow liquid to flow through.

Valves that partition the partitioning channel may be called "partition valves."

The partitioning of the partitioning channel into segments is the mechanism by which individual cells (or cellular units) are physically separated from other cells. Two cells are physically separated when there is a physical barrier interposed between them and the cell are each confined to a unique space. Typically cell capturing is a stochastic process based on random distribution of cells in the partitioning channel.

The partitioning channel may be substantially featureless, or may have secondary features used to position cells to increase the likelihood that segments will contain individual cells (or cellular units). An example of a secondary feature is found in FIG. 17 and Example 5 of US Pat. Pub. 20100120077 describing a "cell comb" that could be used to position individual cells (or cellular units) in a channel (e.g., channel 616) prior to partition. Another example is a channel with significant and periodic differences in width along its length (that, by affecting flow speed, may increase the deposition of particles in the slower regions.

In contrast a substantially featureless channel has generally a constant lumen dimension and shape. Although embodiments with secondary features are contemplated, a substantially featureless partitioning channel is preferred.

As noted, when the valves are actuated, the channel is partitioned into a plurality of segments. Usually the segments are contiguous. In one embodiment the valves are spaced substantially equally along the length of the channel, resulting in segments that are about equally sized.

The number of segments generated can vary across a broad range, e.g., from 10-200, often from 50-100, and sometimes more than 100. Generally there are at least 25 segments, sometimes at least 50 segments, and sometimes at least 75 segments.

The size (volume and dimensions) of the segments can vary over a large range. The segments should be large enough to contain an individual cell but small enough for efficient use of space. Exemplary segment lengths are about 20, about 30, or about 40 microns in length (e.g., about 20 to about 40 microns in length).

In some embodiments, the volume of each segment is many times that of a single target cell. The volume of most eukaryotic cells is in the range of 0.05 picoliter to 4.2 nanoliters.

In another embodiment, the fluid flow does not stop and various cells and a variety of positions are sorted (i.e. parallel shift register). This process requires tight coordination of valve actuation, but has the advantage of faster cell selection of multiple cells in a parallel mode.

6. Cell Concentration

The invention may be used to characterize and combine single cells, single cell units, or combinations. It is desirable therefore that at least some partitioned segments contain a single cell and it is generally advantageous to maximize, to the extent practical, the proportion of partitioned segments that contain a single cell (in contrast to segments that contain no cell or contain multiple cells). The size of segments, concentration of cells, and other factors may be selected to selected to maximize capturing of single cells. An optimal cell concentration for introduction into the partitioning channel, for example, can be determined empirically or can be calculated mathematically.

In determining that a segment contains a single cell, in some embodiments, when the presence of other cells does not interfere with the analysis to be conducted, cells of a particular class are counted. For example, if a solution containing a few eukaryotic cells and a vast excess of bacterial cells is used, some segments will contain a single eukaryotic cell, and some or all segments would likely contain many bacterial cells. In this case a segment containing one eukaryotic cell and numerous bacterial cells may be considered to have a single cell (of the specified class). Similarly, if a solution containing a few nucleated cells and a vast excess of anucleate red blood cells is used, some segments will contain a single nucleated cell, and some or all segments would likely contain many erythrocytes. In some cases, the cell population of interest are (i) all eukaryotic cells, (ii) all nucleated cells, (iii) all animal cells, (iv) all human cells, (v) all prokaryotic cells, (vi) all protozoa, (vii) all parasites, (viii) all fungal cells.

As discussed below, it is contemplated that multiple rounds of cell capturing will be carried out to populate a plurality of cell holding chambers with cells of interest. Preferably, each round of cell capturing results in at least one segment with a single cell. Usually there will be at least one segment with no cell. Preferably at least 30%, alternatively at least 40%, and preferably the majority of segments contain no more than one cell (i.e., they contain one cell or zero cells).

7. Determining at Least One Characteristic of a Captured Cell

One or more characteristics or, equivalently, "properties," of the captured cells (i.e., some or all of the captured cells) are determined while the cells are captured in the segment. Examples of characteristics that may be determined include, for example and not limitation, size, morphology, optical properties (e.g., color, refractive index; see, e.g., Coelho et al., 2006, "Measuring optical and mechanical properties of a living cell with defocusing microscopy," Biophys J. 91:1108-15), presence or absence of an extracellular or intracellular antigen, nucleic acid content, cell membrane electrical properties, mobility, response to stimulus, etc.

The method of determining the characteristic will depend on the specific characteristic(s) detected. For example, cell properties can be determined optically (e.g., using a microscope or CCD camera), spectroscopically (e.g., using Raman spectroscopy), by measuring dielectrophoretic properties (see, e.g., K. Hoettges 2008, "Dielectrophoresis as a Cell Characterisation Tool" in Methods in Molecular Biology 583:183-198), or by detecting a signal (e.g., fluorescent signal) associated with a cell antigen or nucleic acid. Devices for detecting the cell property can be wholly or partly integral to the microfluidic device or may be external to the device. The determination process can manual, or partly or wholly automatic. Exemplary signal detectors monitor visible, fluorescent, and UV light (intensity, scattering, absorption) luminescence, differential reflectivity, electrical resistance, resistivity, impedance, and voltage. Applications can also utilize confocal laser scanning, radiochemical detection, fluorescence polarization and other methods. It will be recognized that the design and materials used in construction of the microfluidic system will be compatible with the mechanism(s) of detection. For example, when optical methods are used, the partitioning channel may be manufactured using materials transparent to at least the wavelengths of light required for detection. Alternatively, fiber optic and other systems may be employed.

Captured cells may be characterized by a combination of more than one characteristic, such as a combination of the presence or absence of a several extracellular antigens, or intracellular biomarkers including antigens (proteins), specific RNA or DNA sequences, or protein presence or activity.

Different populations of cells of interest may be identified by assaying captured cells for two different characteristics, one a characteristic of one population and the second a characteristic of a second population. In one approach at least one detectable label is associated with cells in a population based on a property present in (positive selection), or absent from (negative selection), cells of interest. Suitable immunocytochemical methods for characterizing cells are very well known in the art.

For illustration and not limitation, cell characteristics include three categories of properties, any of which may be used to characterize cells. (1) characteristics of untreated cells; (2) detectable labels associated with cell components; and (3) cell responses to challenges.

Characteristics of untreated cells can include morphology, optical properties, electrical properties, metabolic properties (e.g., $O_2$ consumption), behavior (mobility, membrane ruffling, and the like).

Detectable labels associated with cell components can include detectable labels associated with nucleic acids, cell antigens, and other cell components. A noncomprehensive list of exemplary detectable labels is provided in § 17(B).

Cell responses to challenges refers to detection of a cell property that changes in response to a change in the physical or chemical environment of the cell. For example, captured cells may be exposed to a physical change (temperature change, illumination, pH change, etc.) and the response of the cell detected. As another example, captured cells may be challenged by exposure to a reagent (e.g., drug, test agent, inhibitor, etc.) and the cell response detected.

It will be appreciated that characteristics of untreated cells and cell responses to challenges may be detected using a detectable label. For example, the endocytosis (as a cell property) or increased endocytosis in response to a physical or chemical challenge, can be detected by exposing the cells to incubating the cells with fluorescently labeled polystyrene nanoparticles and detecting update of the fluorescent label.

Cells can be challenged and/or labeled with a detectable label prior to introducing cells into the partitioning channel, after the cells are introduced into the partitioning channel, or both.

For example, in some embodiments at least some cells are detectably labeled prior to introduction into the partitioning channel. In other embodiments, at least some cells are labeled while captured in the channel, e.g., by flowing a detection reagent through the channel. A cell population may be labeled with one label before capturing and labeled with a different label after capturing. A cell population may be labeled by exposing the cell to one reagent before capturing and to a corresponding detectable label after capturing. For example, a cell population may be exposed prior to capturing to a mouse antibody that recognizes a cell surface antigen and then exposed while captured to a rhodamine-tagged anti-mouse antibody to make the cell.

Single captured cells determined to have a property of interest are transported to cell holding chambers. The remaining cells may be discarded, for example, by opening the valves in the partitioning channel and removing the cells and other material not transported to cell holding chambers. In one embodiment, several queries can be made to select cells for transport to cell destination chambers. For example and not limitation, the following quires can be made for each segment:

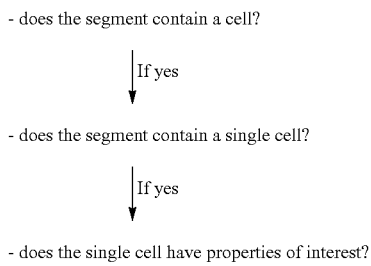

- does the segment contain a cell?

↓ If yes

- does the segment contain a single cell?

↓ If yes

- does the single cell have properties of interest?

8. Multiplexor Channels and Flow Channels Associated with Segments

Captured cells identified as having appropriate characteristics are transported to one of several cell destination chambers (described in § 10 below). Any transport system that permits selected single cells (or single cell units) to be independently transported to specified cell destination chambers may be used. As used in this context, "independently transported" means that an individual cell may be transported from any one of a plurality (e.g., 10-500) of segments to any one of a plurality (e.g., 10-500) of cell holding chambers, allowing selected combinations of cells to be transported to the same cell destination chamber.

Figure 7:
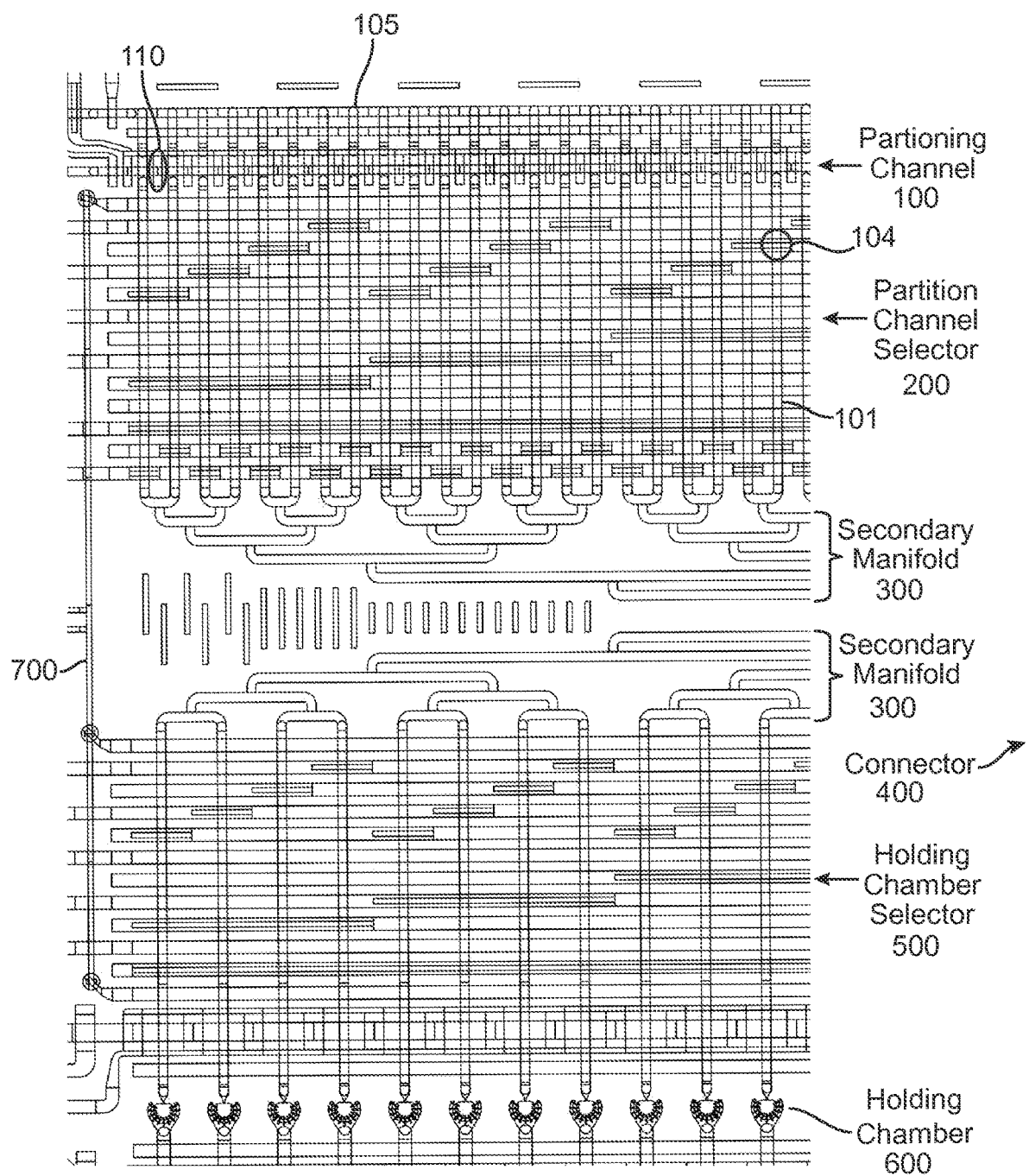
FIG. 7 shows an exemplary design of a device.

In one approach, cells are transported using a compound manifold system. The compound manifold comprises a "combining manifold" and a "distributing manifold" connected by a connector channel X. Each of the segments S of the partitioning channel is in fluid communication with unique combining channel Cc of the combining manifold. Flow through each unique channel Cc can be controlled by actuating selected valves or otherwise controlling flow (or cell movement in the case of electro-osmotic transport) through each channel Cc, so that cells can flow through only a single selected channel Cc. Each channel Cc is fluidically linked to a connector channel X. The combining channels Cc may be linked to connector channel X by a single common channel (as illustrated schematically in FIGS. 2 and 3), by a secondary manifold system (as illustrated in FIGS. 4A, 4B, and 7), by more than one connector, or otherwise. (The terms "combining manifold" or "distributing manifold" encompass the associated secondary manifold systems.) The system is arranged so that when channels are configured to allow particles (e.g., a cell) to flow through only one combining channel Cc, the particles will flow into the connector channel X.

The distributing manifold mirrors, to a degree, the combining manifold. Each of the cell holding chambers H is in fluid communication with unique distributing channel Cd of the distributing manifold. Flow through each unique channel Cd can be controlled by actuating selected valves or otherwise controlling flow (or cell movement in the case of electro-osmotic transport) through each channel Cd, so that cells can flow through only a single selected channel Cd. Each channel Cd is fluidically linked to connector channel X. The combining channels Cd may be linked to connector channel X by a single common channel (as illustrated schematically in FIGS. 2 and 3), by a secondary manifold system (as illustrated in FIGS. 4 and 7), or otherwise. The system is arranged so that when distributing channels are configured to allow particles (e.g., a cell) to flow through only one distributing channel Cd, the particles will flow from connector channel X to only one cell holding chamber H.

It will be appreciated by reference to the figures and description herein that using a compound manifold, a cell can be independently transported from any segment S (i.e., any segment address in the partitioning channel) to any to any cell holding chamber H (i.e., any cell holding segment address.

The "combining manifold" and associated valves, and the "distributing manifold" and associated valves, each can be referred to as a "multiplexor" system.

In one approach, cells are transported using such a compound manifold or multiplexor system. Single multiplexor systems are described in, for example, U.S. Pat. No. 7,143,785, incorporated herein by reference. Also see, T. Thorsen "Microfluidic Technologies for High-Throughput Screen Applications," Ph.D. Thesis, California Institute of Technology, Chapt. 5; and Melin and Quake, 2007, "Microfluidic Large-Scale Integration: The Evolution of Design Rules for Biological," *Automation Annu. Rev. Biophys. Biomol. Struct.* 36:213-31; Hua et al., 2006, A versatile microreactor platform featuring a chemical-resistant microvalve array for addressable multiplex syntheses and assays. J Micromech Microeng 16:1433-1443; each incorporated herein by reference. Microfluidic multiplexors can switch flow from a plurality of individually addressable inputs (channels) to a single output, or switch flow from a single input to a plurality of individually addressable outputs.

Optionally the multiplexor system includes a shift register. (See Sai et al., 2102, "Pressure driven digital logic in PDMS based microfluidic devices fabricated by multilayer soft lithography" Lab on a Chip 12, 4809-4815; DOI: 10.1039/c2lc21155f). Optionally, the multiplexor system operates by control signals generated by a shift register wherein the shift register is controlled by an user-settable input, a repeating 'clock', and a trigger valve. The user-settable input provides serial input instructions that are 'read' into the shift register, moving the input signal one 'bit' through the register per 'clock' cycle. The trigger valve serves to open communication between the pneumatic shift register outputs and the fluidic multiplexor 'control' channels.

Figure 3A:
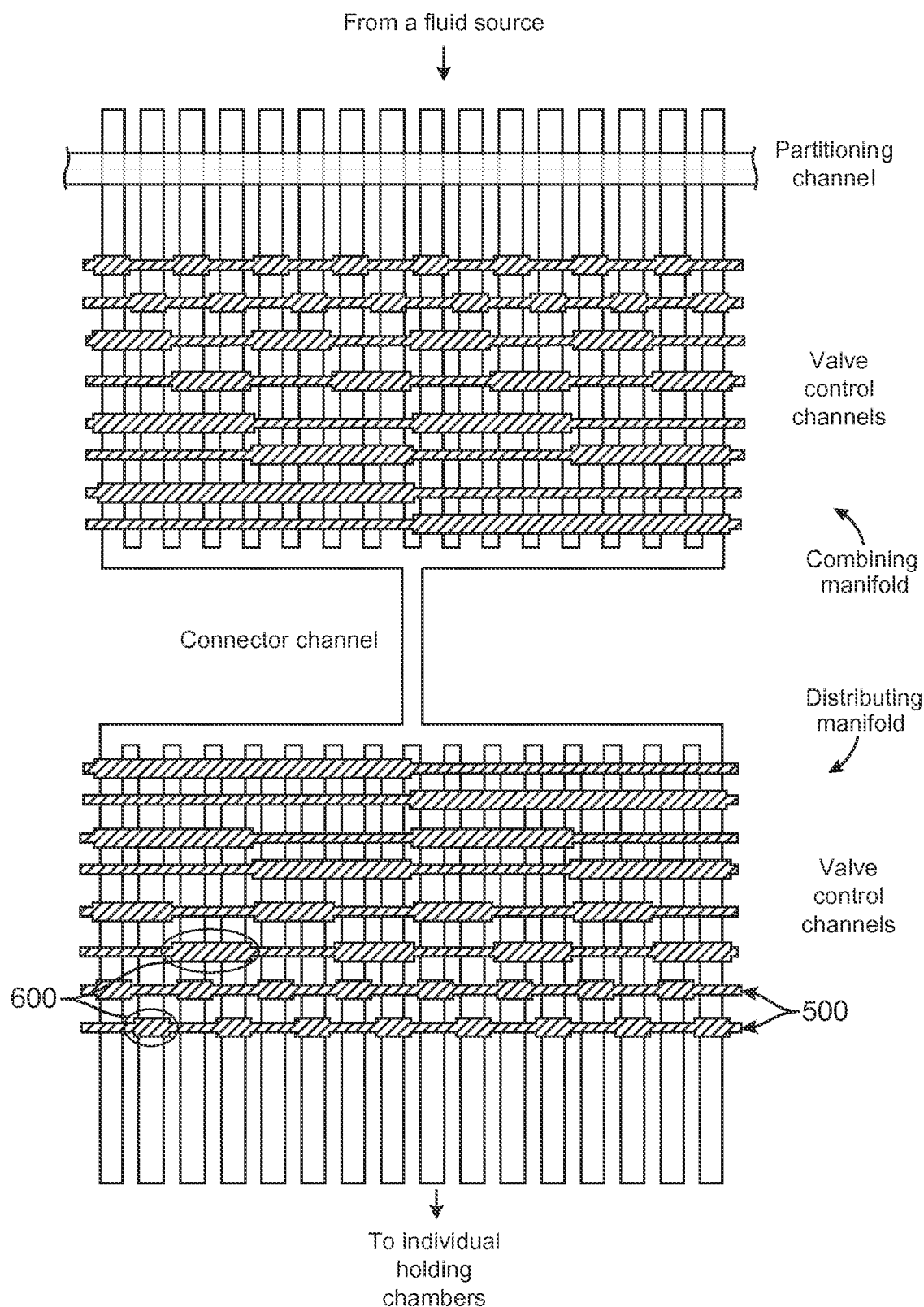
FIGS. 3A and 3B illustrate the principal of multiplexors that may be used to independently transport a single cell from any segment to any predetermined destination chamber.
Figure 3B:
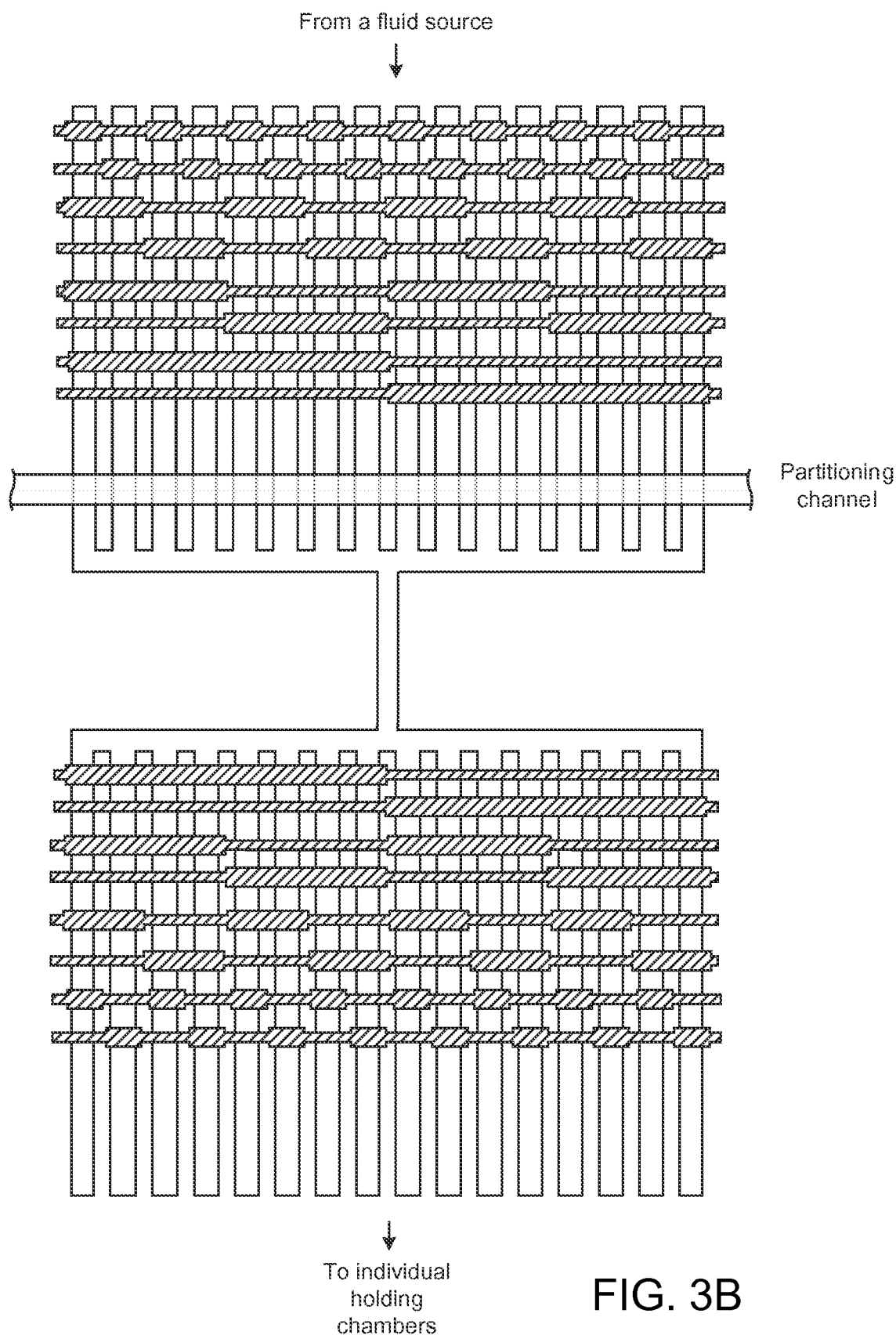
Figure 4A:
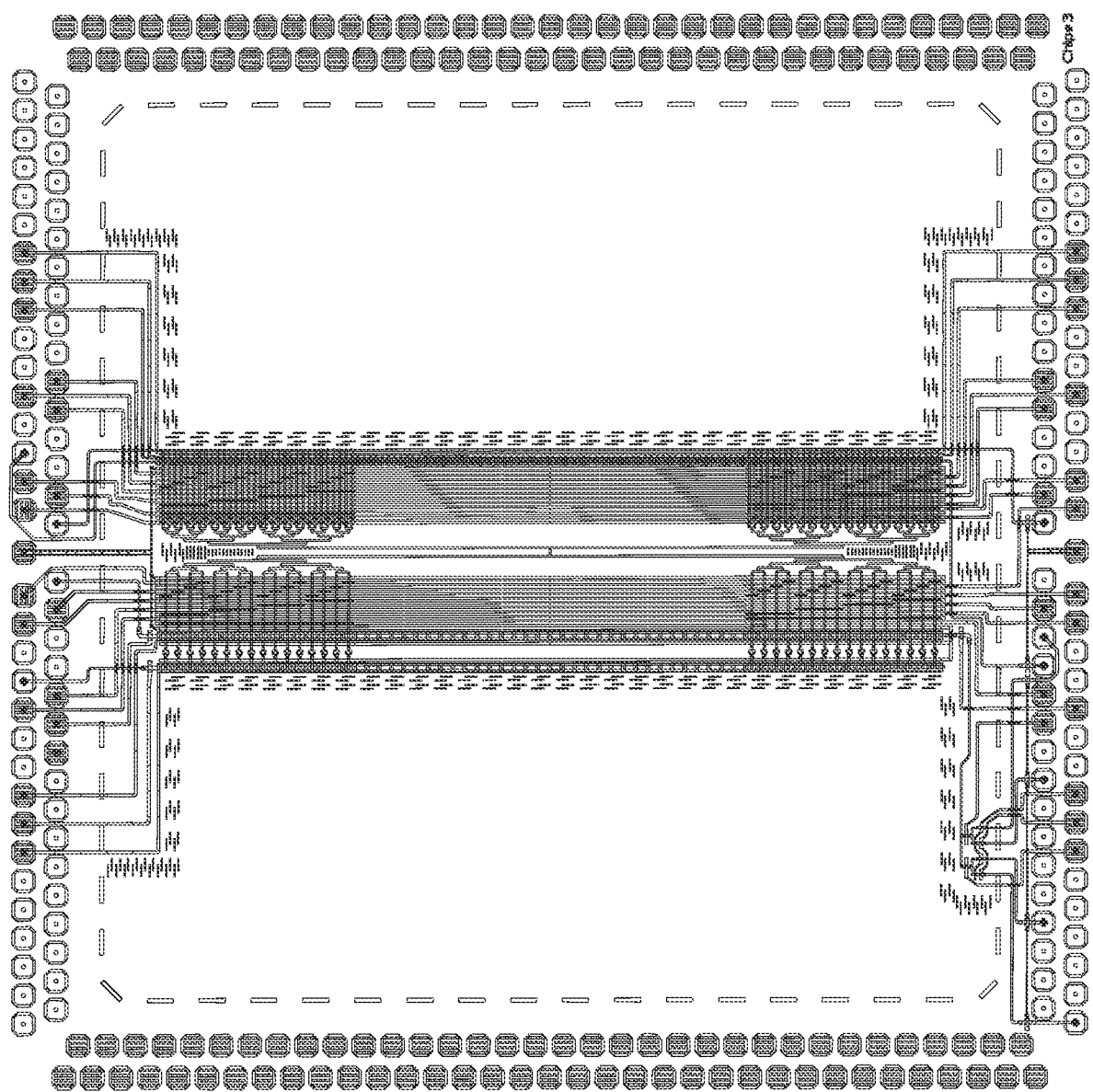
FIG. 4A shows a fluidic system in which channels of the combining manifold, and similarly channels of the distributing manifold, are separated into two blocks, each block remaining connected via the secondary manifold systems to provide a single unified combining manifold and, similarly, a single unified distributing manifold connected by a connector channel.
Figure 4B:
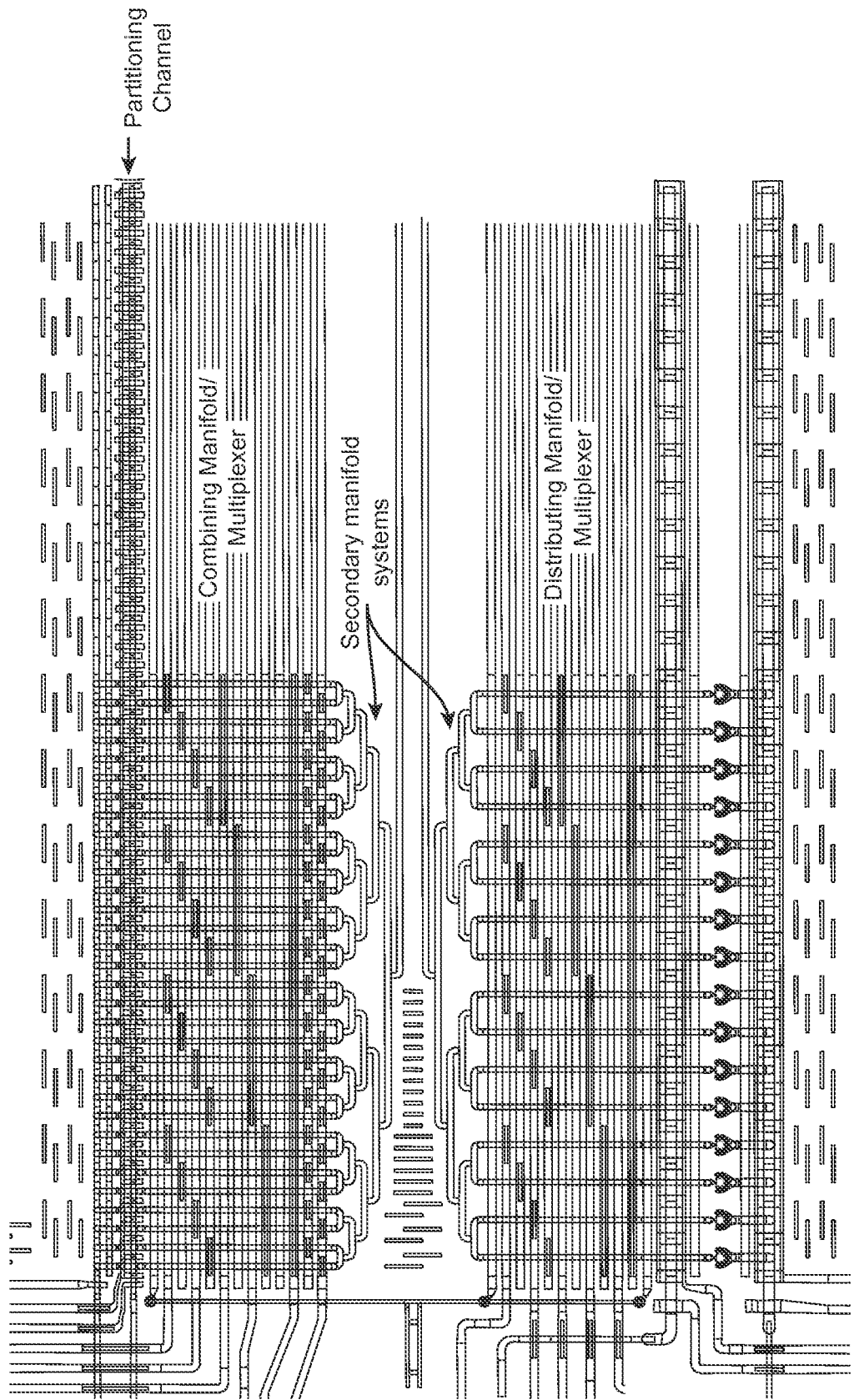
FIG. 4B is a detail from FIG. 4A.

FIGS. 3A and 3B illustrate the principal of a multiplexor system of the invention. In these figures, elastomeric valves actuated by control channels 500 are represented. See Unger et at., 2000, "Monolithic microfabricated valves and pumps by multilayer soft lithography" Science 288: 113-116. In the cartoon the control channels have wider regions and narrower regions. Valves 600 are created where a wide section of a control channel crosses over (or under) a fluidic channel. By actuating selected combinations of control channels paths may be created from any segment to any cell holding chamber. It will be appreciated that the valve pattern in FIGS. 3A and 3B are for illustration and that a variety of other patterns could be used. See, e.g., FIG. 7. The elastomeric system is highly efficient and allows control flow through n fluid channels using <n control channels. However, it will be appreciated that the method is not limited to elastomeric embodiments. Virtually any number of valves that substantially completely stop fluid flow could be used. For example, in one approach flow through each multiplexor channel can be controlled by an independently actuatable valves, and flow can be controlled by, for example, closing all but one valve in the partition chamber sector and all but one valve in the holding chamber sector.

In one embodiment, bulk fluid flow is used to transport selected cells from a segment to a cell holding chamber. For illustration, with reference to see FIG. 5, each partitioning channel segment is in fluid communication with a multiplexor channel 107 and a flow channel 105. The multiplexor channel may be a downstream multiplexor channel (FIG. 3A, FIG. 7) or an upstream multiplexor channel (FIG. 3B). The flow channel 105 may be an upstream flow channel (FIG. 3A, FIG. 7) or a downstream flow channel (FIG. 3B). Downstream channels lie between the partitioning channel and the cell destination chambers. In each approach, the downstream channel has appropriate dimensions and is otherwise suitable for carrying cells (i.e., cells flow through the downstream channel). In contrast, the upstream channel provides liquid that facilitates flow of the cell into the downstream channel. It will be recognized that a downstream multiplexor channel is used with an upstream flow channel and vice versa.

Following partition, a cell may be transported by a fluid stream following the path: (1) fluid source→(2) upstream channel→(3) segment→(4) downstream channel→(5) connector (e.g., connection manifold)→(6) holding chamber sector flow channel→(7) cell holding chamber→(8) (optionally) multi-chamber reaction configuration.

Figure 5:
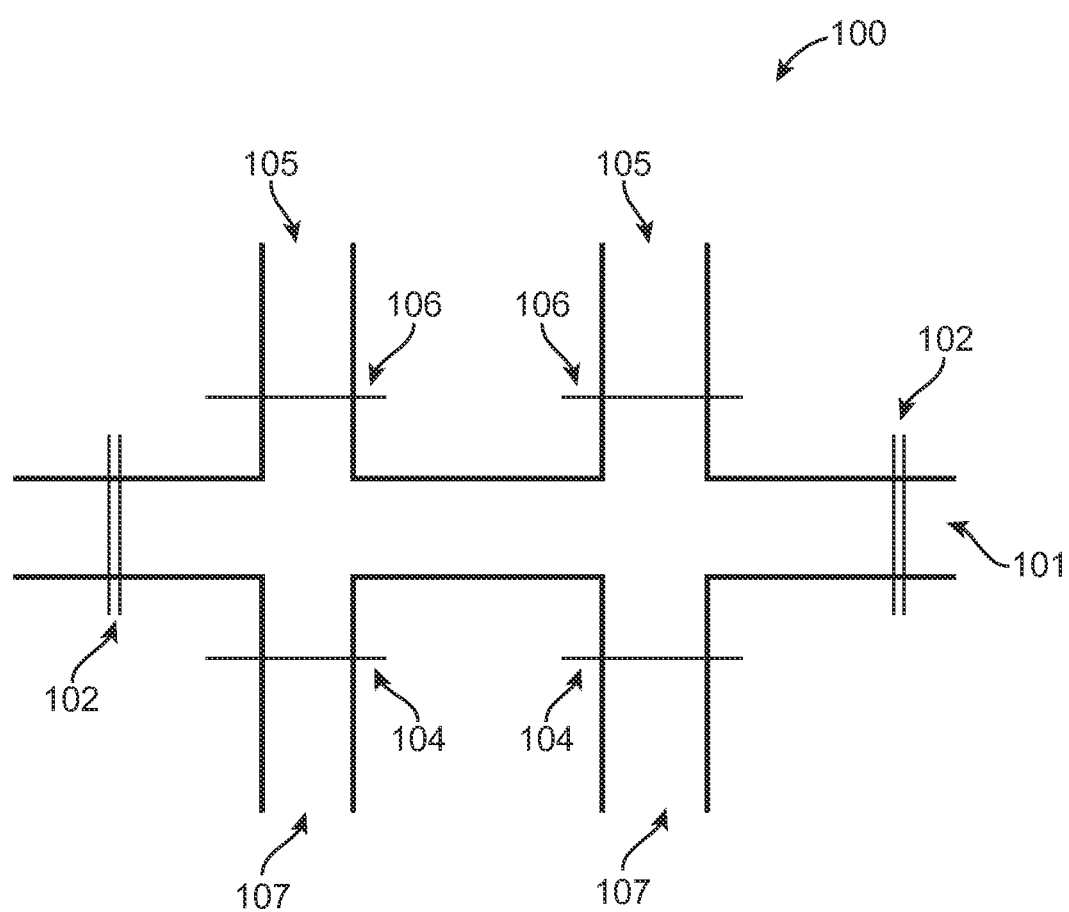
FIG. 5 illustrates a relationship, in one embodiment, of a segment, a flow channel and a multiplexor channel.

As illustrated in FIG. 5, in addition to valves used to effect the longitudinal separation resulting from partition of the partitioning channel, additional valves may be optionally used to control flow of cells into upstream channels (upstream valves 106) and/or downstream channels (downstream valves 104). For example, cells may be flowed through the partitioning channel with partition valves 102 open, and valves 104 and 106 may be closed to prevent the cells from flowing into upstream and downstream channels. Alternatively upstream and/or downstream channels may not have valves. For example, upstream channels may have channel dimensions or geometry that prevent a cell from entering the channel. In another approach, they may have channel filters which allow liquid to flow through them but block passage of cells. In another approach, in the case of an upstream multiplexor, the multiplexor valves when closed will block the upstream channel. In this case, even if cells migrate into the upstream channels they can be transported out of those channels, either to a destination chamber or to waste. It will be recognized that this design may make the step of removal of unselected cells more complex. In another approach, channel dimensions can be selected to render upstream and/or downstream valves unnecessary. This is because, during the loading step in which cells are flowed into the partitioning channel, there will be flow though the partitioning channel but no flow ("static flow") through the rest of the system; as a result cells flowing through the partitioning channel tend not to drop into upstream or downstream channels, which are occupied by fluid.

Generally each segment is in communication with a different (unique) multiplexor channel. Alternatively, it is possible to use manifolds connecting pairs of segments so that pairs or multiples of channels are connected to a distributing multiplexor channels (used, for example, when only one segment of a connected pair comprise a target cell) although such designs generally require a sacrifice in efficiency.

FIG. 7 illustrates an exemplary design of the multiplexor system. The system comprises partitioning channel 100, partitioning valves 110, upstream flow channels 105, partitioning channel selector (multiplexor) 200 comprising downstream multiplexor channel 101 and downstream valves 104, secondary manifold systems 300, connector 400 (not shown), cell holding chamber channel selector (multiplexor) 500, and cell holding chambers 600. Also shown are control channels 700 controlling containment valves.

In contrast to the schematic multiplexor shown in FIG. 3, secondary manifold systems are shown in FIG. 7. The manifolds ensure that the distance (and approximate transit time) between any segment and any cell holding chamber is the same. This uniformity has the advantage of maintaining a consistent actuation time and routines between valved partitions that are transporting a cell from any segment to any cell holding chamber.

Figure 14:
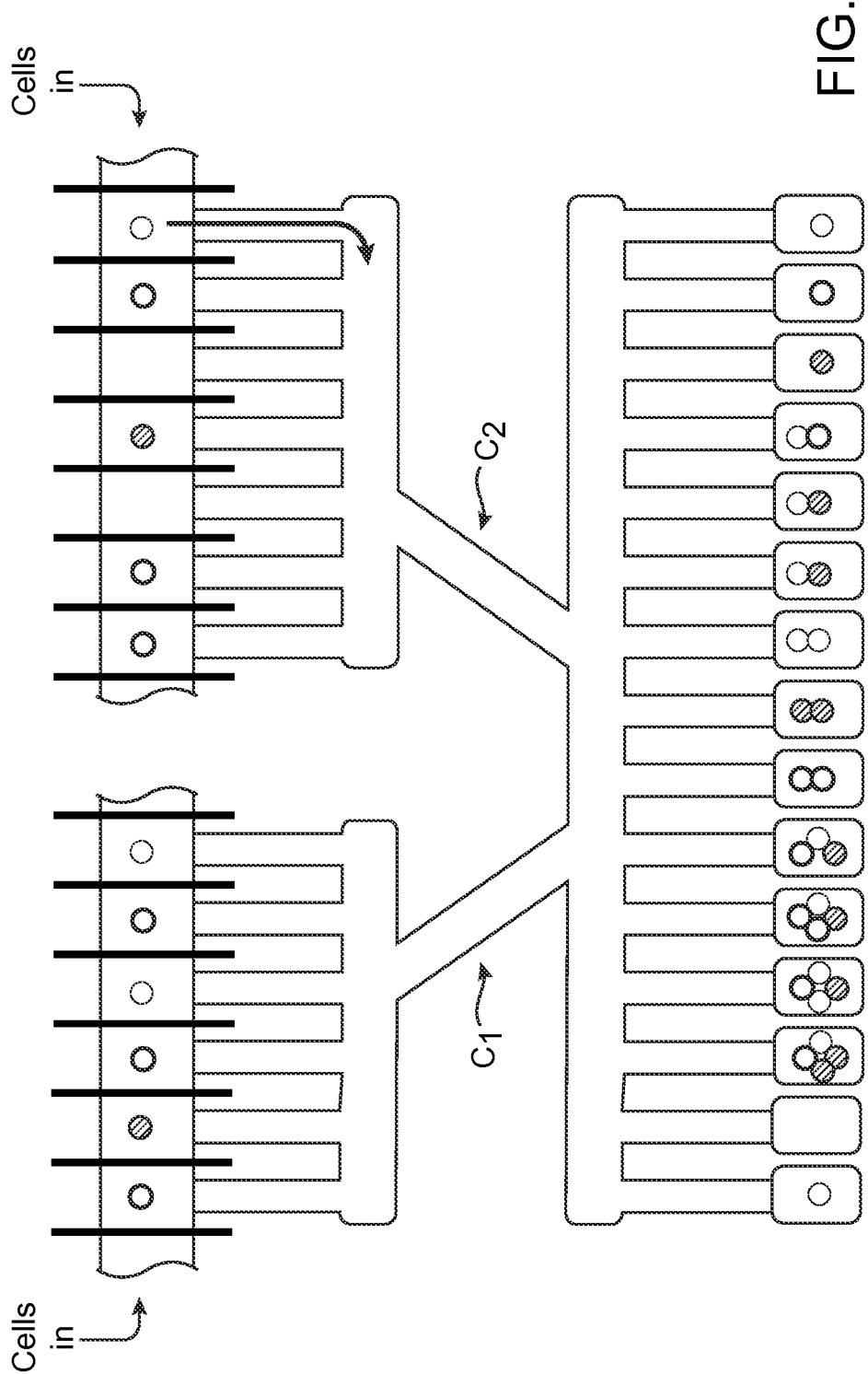
FIGS. 14 and 15 illustrate embodiment in which more than one connector channel is used.
Figure 15:
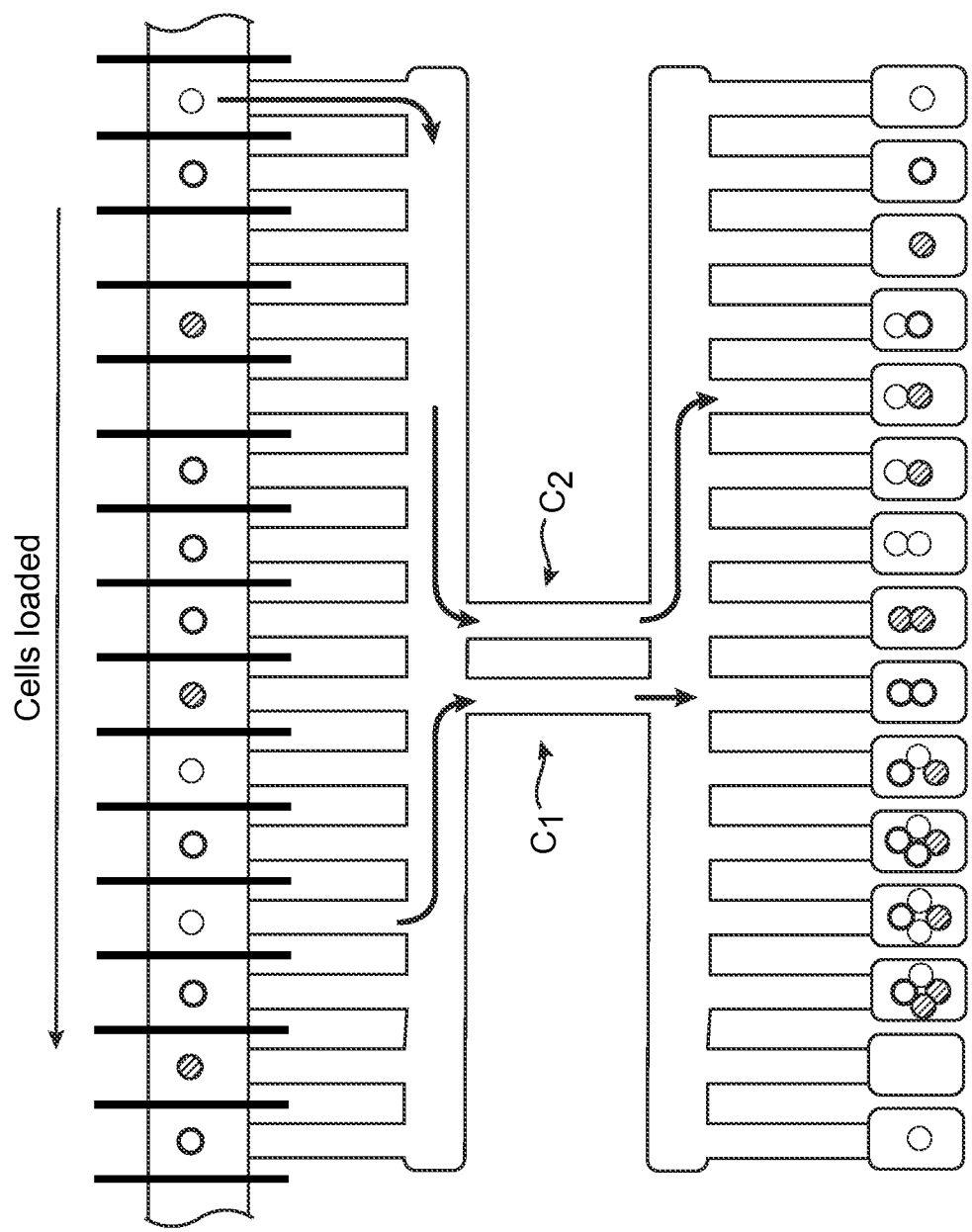

FIGS. 14 and 15 illustrate embodiment in which more than one connector channel is used. In FIG. 14 each of two combining manifolds is connected by a separate connector ($C_1$ and $C_2$) to a single distribution manifold (compare FIG. 2B). FIG. 15 illustrates a system with two connectors, $C_1$ and $C_2$. At time N, a cell is transported through $C_1$ and enters a cell holding chamber. At time N+1, a different cells is transported through $C_2$ and enters a different cell holding chamber.

Figure 12:
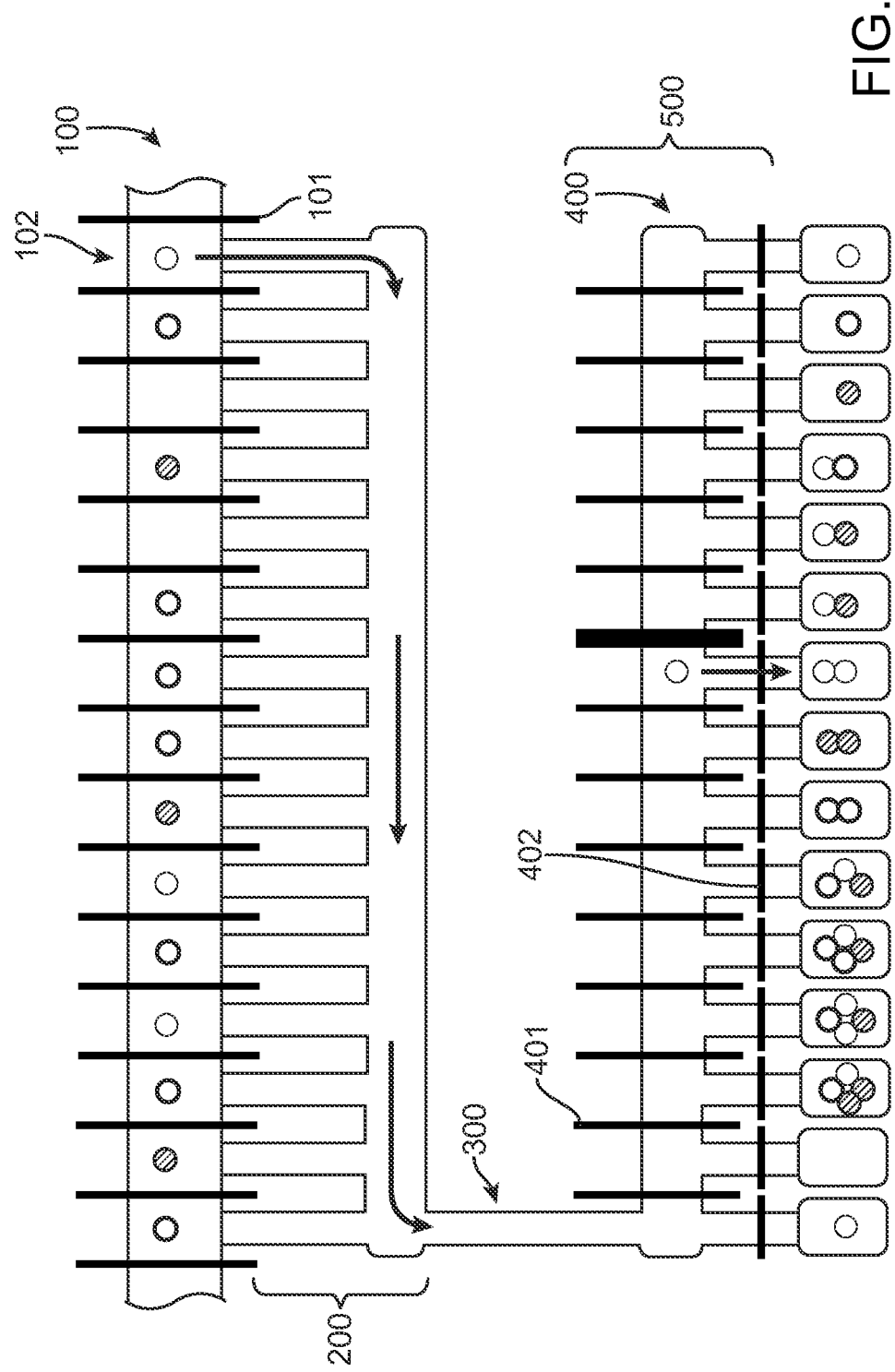
FIGS. 12 and 13 show an alternative path for transporting a cell from a segment to a cell holding chamber.
Figure 13:
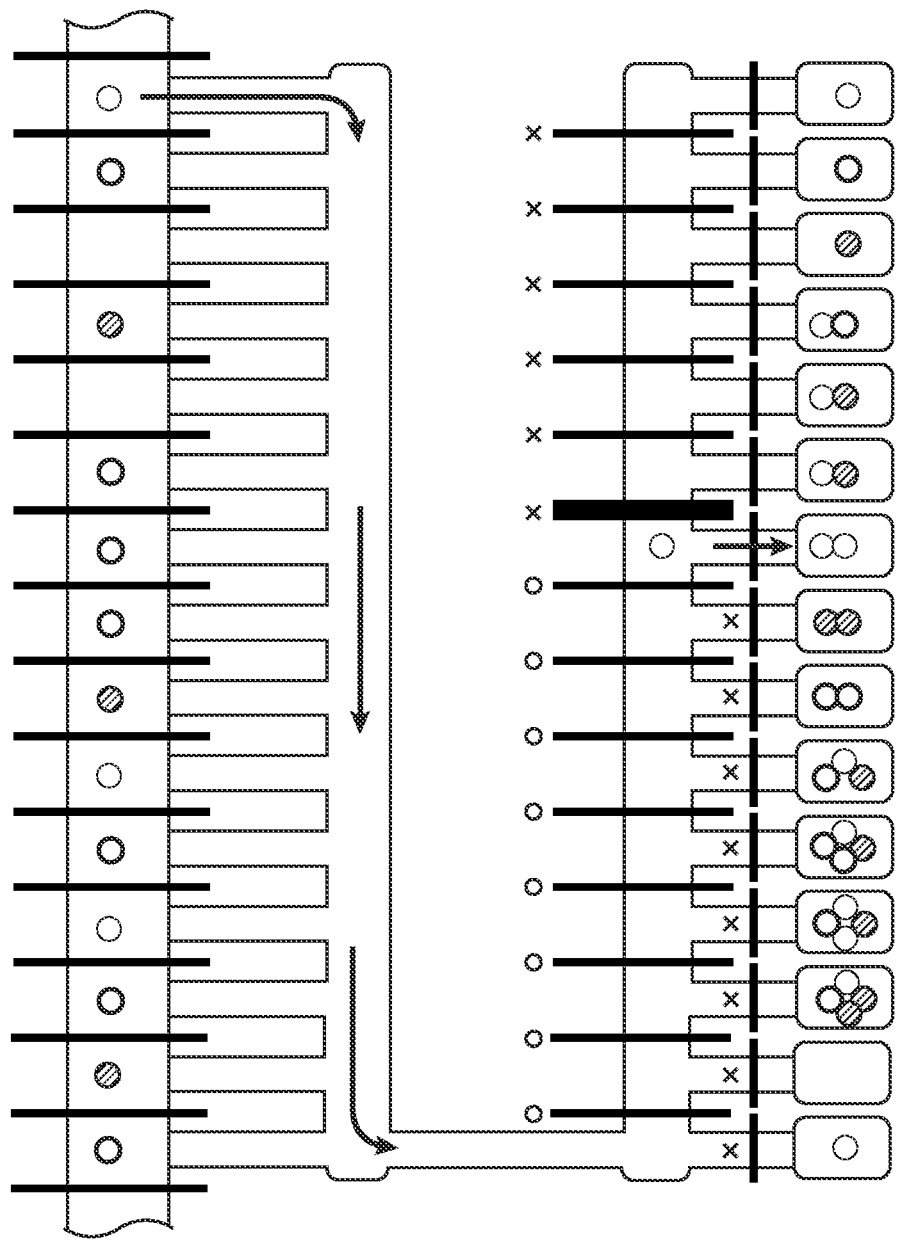

Another approach for transporting cells from a segment to a cell holding chamber is illustrated in FIG. 12. In this approach cells are introduced into a partitioning channel 100 and confined to segments 102 by partitioning valves 101, as described above. The content of a selected segment (i.e., a selected single cell or group of cells). Selected cells are transported through a combining manifold 200 to connector 300, generally as described above. The approach illustrated in FIG. 12 differs from that of, e.g., FIG. 7 in the transport of cells from the connector to a specified cell holding chamber through the distributing manifold 500. As shown in FIG. 12, the connector channel is connected to a "second partitioning channel." To avoid confusion, this second partitioning channel is referred to as the "stop channel" 400 but the features of the stop channel are analogous to those of partitioning channels described above. The stop channel comprises independently controllable stop valves 401 and CHC valves 402. FIG. 13 illustrates how, by actuating a selected stop valve and selected CHC valves, flow is directed to a specific cell holding chamber (arrow). In FIGS. 12 and 13 one stop valve is thickened to illustrate that it is closed such that a cell is directed towards a particular chamber.

9. Flowing

Fluid and cells may be transported into and though channels in a variety of ways known in the art. In general, transport of cells in the present invention occurs by bulk flow (i.e., the cells are carried in a stream of moving fluid).

Flow of solution can be accomplished by a variety of methods. For illustration, the solution may be introduced by pumping (e.g., using a peristaltic pump as described in U.S. Pat. No. 6,408,878, incorporated herein by reference), by generating a positive pressure differential in the channel (e.g., cells may be introduced into the partitioning channel from a syringe by depressing the plunger thereby creating a pressure differential) or a negative pressure differential (e.g., a syringe may be used to draw out fluid from a channel, causing flow through the channel), by gravity driven flow, or any other method.

In alternative embodiments cells are moved using electrophoretic, electrokinetic, or electro-osmotic methods. (see, e.g., Glawdel and Ren, 2009, "Electro-osmotic flow control for living cell analysis in microfluidic PDMS chips" *Mechanics Research Communications* 36: 75-81, incorporated herein by reference).

10. Cell Holding Chambers and Cell Culture

10.1. Cell Holding Chambers

Systems of the invention have cell holding chambers for culture of individual cells (or cellular units) and combinations of cells captured, characterized and transported as described hereinabove. The number of cell holding chamber may vary over a wide range, but is typically in the range of 10-500, more often 100-500, more often 150-400, and often about 300 microns. The number of cell holding chambers may be smaller than, equal to, or greater than the number of segments. Generally the number of cell holding chambers is smaller.

Minimum attributes of microfluidic cell holding chambers are two-fold: The chamber has to be large enough to contain at least one cell, and preferably at least 2-10 cells, and the chamber has to be compatible with cell viability. The requirements for viability will vary from cell to cell (e.g., a human tumor cell will differ from a human hepatocyte or an algal cell), but typically the chamber must be maintained at an appropriate temperature and humidity, nutrients must be provided the cell(s), and waste products must be removed to the extent required for viability. The chambers typically include an inlet and an outlet to allow fluid flow in and out of the chambers. Nutrients that support cell growth can be either supplied from the inlet or the outlet channel.

Some or all of the surfaces of a culture chamber, such as the walls, roof, and/or substrate, may be treated or modified to facilitate aspects of cell culture, particularly specific or nonspecific cell attachment, cell survival, cell growth, and/or cell differentiation (or lack thereof), among others. The cell holding chamber surface or base can be modified to include a surface that supports cell growth, mimicking the extracellular matrix (ECM) of a tissue. Examples of typical ECMs include, but are not limited to, fibronectin, collagen, elastin, laminin, hyaluronic acid, heparan sulfate, chondroitin sulfate, keratan sulfate.

The cell culture mechanism may culture cells under any suitable environmental conditions using any appropriate environmental control mechanisms. Suitable environmental conditions may include a desired gas composition, temperature, rate and frequency of media exchange, and/or the like. Environmental control mechanisms may operate internal and/or external to a microfluidic system. Internal mechanisms may include on-board heaters, gas conduits, and/or media reservoirs. External mechanisms may include an atmosphere- and/or temperature-controlled incubator/heat source, and/or a media source external to the system. An atmosphere-controlled incubator may be more suitable when the system is at least partially formed of a gas-permeable material, such as PDMS.

Culture chambers may have any shape or composition consistent with the requirements above.

10.2. Exemplary Cell Holding Chambers

Figure 6A:
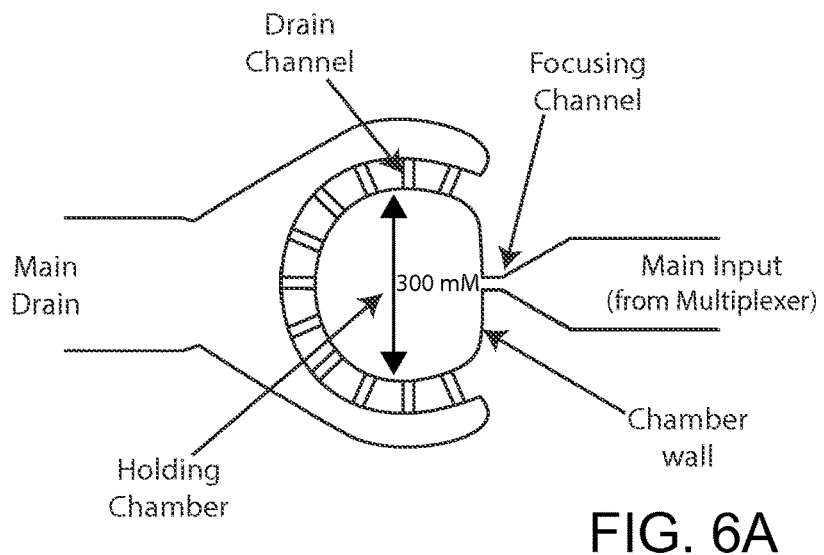
FIGS. 6A-6C show exemplary designs of destination chambers.
Figure 6B:
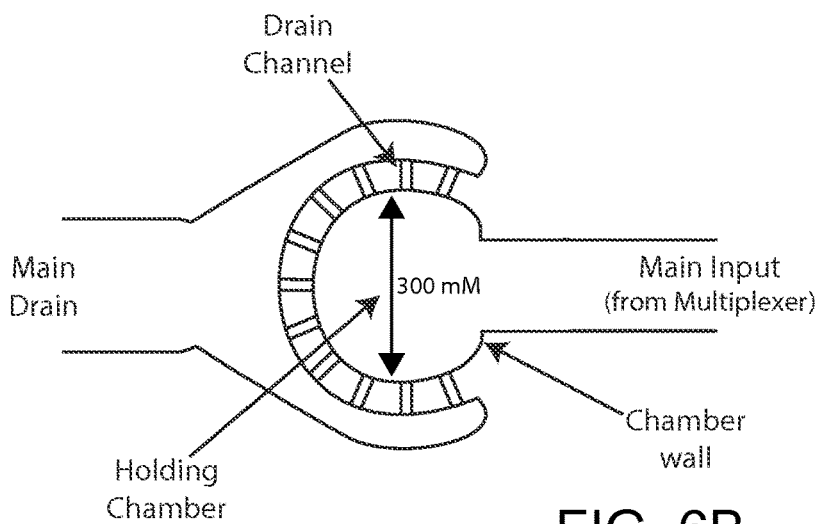
Figure 6C:
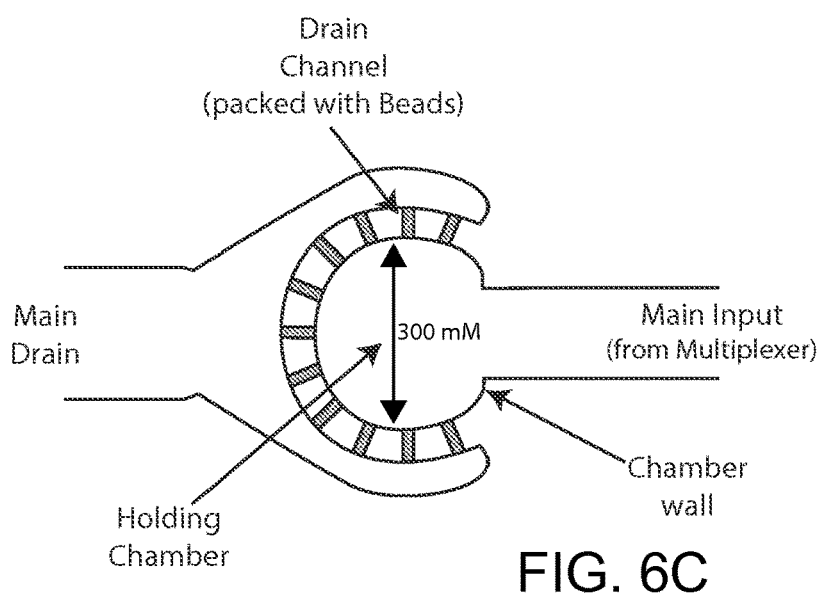

FIGS. 6A, 6B and 6C show exemplary arrangements for a cell holding chamber of this invention. The chamber is configured so that fluid containing cells flow through an input channel, and one or more drain channels act as an outlet that operates selectively to allow fluid to drain but not cells. The holding chambers depicted here are substantially round or circular in shape, with a plurality of drain channels positioned around more than 180 degrees of the holding chamber, connected to a common output.

In some embodiments, the holding chambers of this invention may be 50 microns to 2 mm in diameter, or between 100 and 500 microns in diameter. The dimensions are chosen according to the size and number of cells the operator wishes to process in each chamber. For culturing or maintenance of live cells, the holding chambers have a gas permeable membrane (typically above or below the chamber) so that the partial pressure of gasses in the fluid may be maintained and adjusted appropriately. The holding chambers may also be provided with a surface that promotes cell adherence, such as an extracellular matrix (ECM) of proteins such as fibronectin and/or collagen, or a protein mixture produced from a cell line.

FIG. 6B shows a suitable arrangement of input and drain channels (showing a holding chamber that is 300 microns in diameter). FIG. 6C shows an arrangement where the drain channels have been packed with beads (i.e., "channel filters") to further inhibit cells from flowing from the holding compartment to the drain.

FIG. 6A shows an arrangement where the input channel from the multiplexer tapers towards the holding chamber to form a focusing channel. This configuration focuses each cell being delivered to the holding chamber, such that the cell tends to flow or migrate towards the center of the chamber. Distribution of a plurality of drain channels about the periphery of the chamber also helps maintain the cells at or near the center of the chamber. This configuration tends to keep cells at or near the center of the holding chamber, since draining is diffuse and the cells are not pulled towards the drain. In addition the ability to confine the cells to these chambers is enabled by a combination of elements including flow restrictors at the inlet (A), and/or at the outlet (A and B). In addition the use of porous-to-liquid material, at the outlet drains can be employed to prevent cells from exiting the chamber (C) The ability to control the fluid volume, pressure and sheer are important considerations to enabling cell viability. A third means for urging cells towards the center of the chamber is a concave shape in the lower or supporting surface of the chamber upon which the cells are cultured. Positioning the cells at or near the center of the chamber helps cells interact.

Cell culture media may be introduced into cell holding chambers through the same path taken by cells or through other channel. For example, with reference to FIG. 6, media may be introduced via a main input. Alternatively, media and other solutions may be introduced through other routes, such as via a branch channel that joins the input channel.

Figure 11:
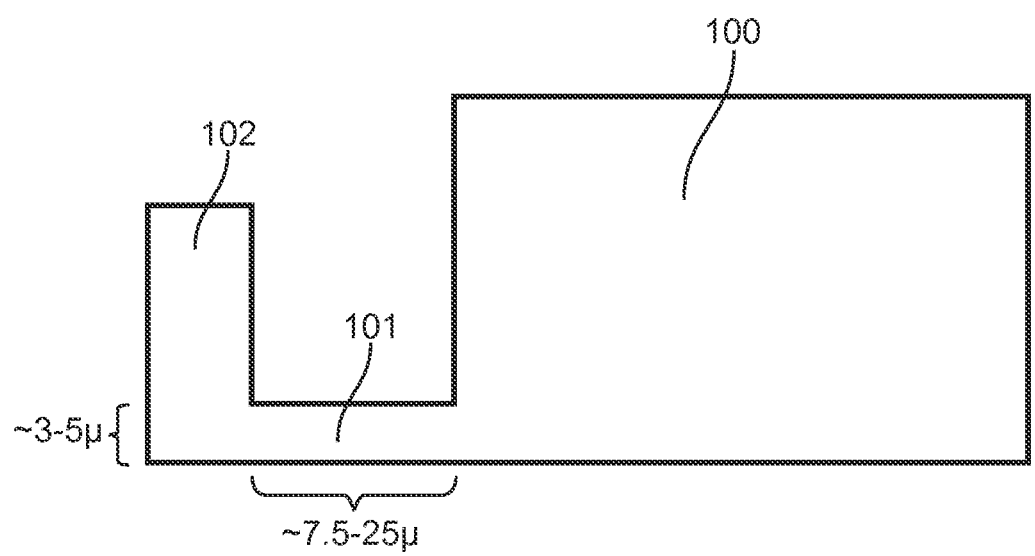
FIG. 11 shows an illustrative diagram of a drain.

Drain channels are preferably openings low on the "wall" on the bottom surface ("floor) of the cell holding chamber 100, but it is contemplated that they could be positioned elsewhere (e.g., on the floor of the chamber). As shown in FIG. 6 and FIG. 11, the drain 101 connects to the main drain 102. Preferably the length of the drain is short (e.g. about 7.5 to about 25 microns). The width may be in the range, for example, of about 10 to about 25 microns, and the height of the drain channel is preferably low (generally less than about 5 microns, sometimes less than about 4 microns, such as about 3 microns). To main drain to which the drain channel connects is designed to have low fluidic resistance and may have dimensions of 10-60 microns×20-40 microns. One design for a drain channel is shown in FIG. 11.

10.3 Introduction of Agents into Cell Holding Chambers

The system of the invention provides a powerful way to study the effects of cell interactions (or co-culture) on metabolism, protein expression, and the like. In addition to media and nutrients, it will sometimes be useful to add other agents to the cell holding chamber, to assess the response of the cell or cell combination to the agent(s) and/or to provide reagents for assay of cell activity and the like. It will be appreciated that a variety of agents may be used, for example and not limitation, chemical modulators or biological modulators, drugs, potential drugs (test agents), pathogens, proteins, antibodies, nucleic acids (e.g., DNA, RNA, modified nucleic acids, sense/antisense expression vectors, reporter genes, vectors for genomic integration/modification antisense oligonucleotides, dsRNA, siRNA). Reagents for detection/assay reagents include, for illustration and not limitation, dyes, enzymes, substrates, cofactors, ligands, antiligands, transfection reagents (e.g., lipid reagents, calcium phosphate, DMSO), polyethylene glycol, viral coats that package the nucleic acids, and/or so on.

10.4. Environmental Control

The environment of cell holding chambers is appropriate for the viability of the cell type(s) being cultured, including appropriate temperature, humidity, pH, and gas composition.

10.5. Cell Culture

Microfluidic technology for culturing cells has been described elsewhere. See Gómez-Sjöberg et al., 2007, "Versatile, fully automated, microfluidic cell culture system" Anal Chem. 79:8557-63; Zhong et al., 2008, "A microfluidic processor for gene expression profiling of single human embryonic stem cells," Lab Chip. 8:68-74; Glotzbach et al., 2011, "An information theoretic, microfluidic-based single cell analysis permits identification of subpopulations among putatively homogeneous stem cells," PLoS One 6:e21211; Sanchez-Freire et al., 2012, "Microfluidic single-cell real-time PCR for comparative analysis of gene expression patterns," Not Protoc. 7:829-38; U.S. Pat. No. 7,378,280 "Apparatus and methods for conducting assays and high throughput screening;" US 2010/0255471 "Single cell gene expression for diagnosis, prognosis and identification of drug targets." The aforelisted publications are hereby incorporated herein by reference in their entirety for all purposes.

11. Rounds

It is contemplated that practice of the invention for analysis of individual cells (or cellular units) and combinations of cells will usually involve multiple rounds of flowing a solution comprising a plurality of individual cells (or cellular units) into a length of a first microfluidic channel; partitioning the length into a plurality of contiguous segments thereby capturing at least one cell in at least one segment; determining at least one characteristic of one or more of the single captured cells; and independently transporting captured cells to cell holding chambers. The number of rounds of capture will vary over a wide range and will depend in part in whether the cells of interest are rare in the population of cells. Generally the number of rounds is in the range of 2-1000. In exemplary embodiments the method comprises at least two, at least three, at least 4, at least 5, at least 6, at least 7, at least 8, or at least 9 rounds. In exemplary embodiments the method comprises 2 to 10 rounds, 3 to 10 rounds, 4 to 10 rounds, or 5 to 10 rounds. In one embodiment the method comprises more than 50, more than 100 or more than 200 rounds of capture and selection.

12. Discarding Cells

Between rounds, unselected cells remaining in the partitioning channel after transport of selected cells to cell holding chambers can be removed. One approach is to "purge" the channel with media or buffer, displacing the solution containing unselected cells from the partitioning channel and into, e.g., a waste reservoir. Alternatively, the unselected cells can be displaced by the action of flowing the solution comprising a plurality of individual cells (or cellular units) into the partitioning channel.

13. Cell Interactions

Based on the determined property, captured cells are independently transported to specified cell holding chambers. "Independently transported" means that each individual captured cell can be transferred to a specified destination chamber according to the needs of the practitioner. Cells can therefore be transported so that the characteristics of each cell or combination of cells in each destination chamber can are known. Typically (but optionally) cells are cultured in the cell holding chambers. The effect of Interactions between individual cells (or cellular units) with known properties (e.g., of know cell types), and/or their progeny, can be studied.

Tables 1 and 2 illustrate this by imagining a device with 4 Segments (1-4), 5 Cell holding chambers (1-5), and two cell types (A and B). In this hypothetical, after six rounds of cell capturing, determination and transport are carried out, as summarized in Table 1, cells are distributed to Cell holding chambers 1-5 are shown in Table 2.

TABLE 1

| Round (6 rounds) | Cell Property | Segment (4 segments) | Destination Chamber (5 chambers) |
|---|---|---|---|
| 1 | A | 4 | 1 |
| 1 | A | 3 | 3 |
| 2 | B | 4 | 2 |
| 3 | A | 1 | 3 |
| 4 | B | 2 | 3 |
| 4 | B | 3 | 4 |
| 5 | B | 1 | 4 |
| 6 | A | 4 | 5 |

As illustrated in Table 2, after two days of culture a gene expression pattern (e.g., expression of k-ras) can be determined for the cells in each of the cell holding chambers. In the hypothetical results shown in Table 2, the effect of interactions of cell type A and cell type B is increased expression (by one or both of the cell types) of the K-ras gene.

TABLE 2

| Chamber | Seed Cell(s) | Gene Expression Pattern After 2 Days Culture |
|---|---|---|
| 1 | A | Low |
| 2 | B | Low |
| 3 | A + B | High |
| 4 | B + B | Low |
| 5 | A + A | Low |

The number of cell holding chambers associated with a partitioning channel (or pair of partitioning channels) can vary but is typically in the range 1-150, more often 10-100, and often 35-75.

Other properties of cell holding chambers, and cell culture in them, are discussed below.

14. Harvest

Cells may be cultured in the cell holding chambers for a desired period of time (e.g., 1 hour to 4 weeks). Typically, short term culture is used (e.g., 1 hour to 24 hours). During culture cells may be observed and, optionally, cells may be manipulated or challenged. For example, cells may be contacted with microRNAs to effect transdifferentiation. In some embodiments the cells either captured or in culture can be assayed with components that result in a change of extracellular or intracellular detectable signals such as a colorimetric or fluorescent molecule. At the end of the culture period, the cells may be discarded, recovered as viable cells, or lysed or otherwise made non-viable for analysis.

14.1. Cells Recovered as Viable Cells

Viable cells may be recovered from the cell-holding chambers in a number of ways. In one approach the cell(s) are enzymatically detached from the substrate, if necessary, and then flowed out of the cell holding chamber for collection. The flow path can be, in principle, the reverse of the path by which cells were transported into the cell holding chamber. Alternatively, an auxiliary exit channel can be used.

In another approach the system is configured to be easily disassembled to expose the cell holding chambers, allowing the contents to be removed (e.g., using a micropipette). In one approach adherent cells are removed by moving the substrate to which the cells are adhered out of the microfluidic system.

14.2. Analysis of Cell Components

In some embodiments, following a culture period, the cell(s) in a cell holding chamber are processed (e.g., lysed) to release cell components such as nucleic acids, proteins and the like. With reference to FIG. 6, a lysis solution can be introduced through the main input or, alternatively, through an auxiliary channel (not shown). Cell components can then be carried into the "main drain" for collection and analysis. The ordinarily skilled practitioner guided by this disclosure will be able to design analogous structure when cell holding chambers with different designs are used.

Figure 8:
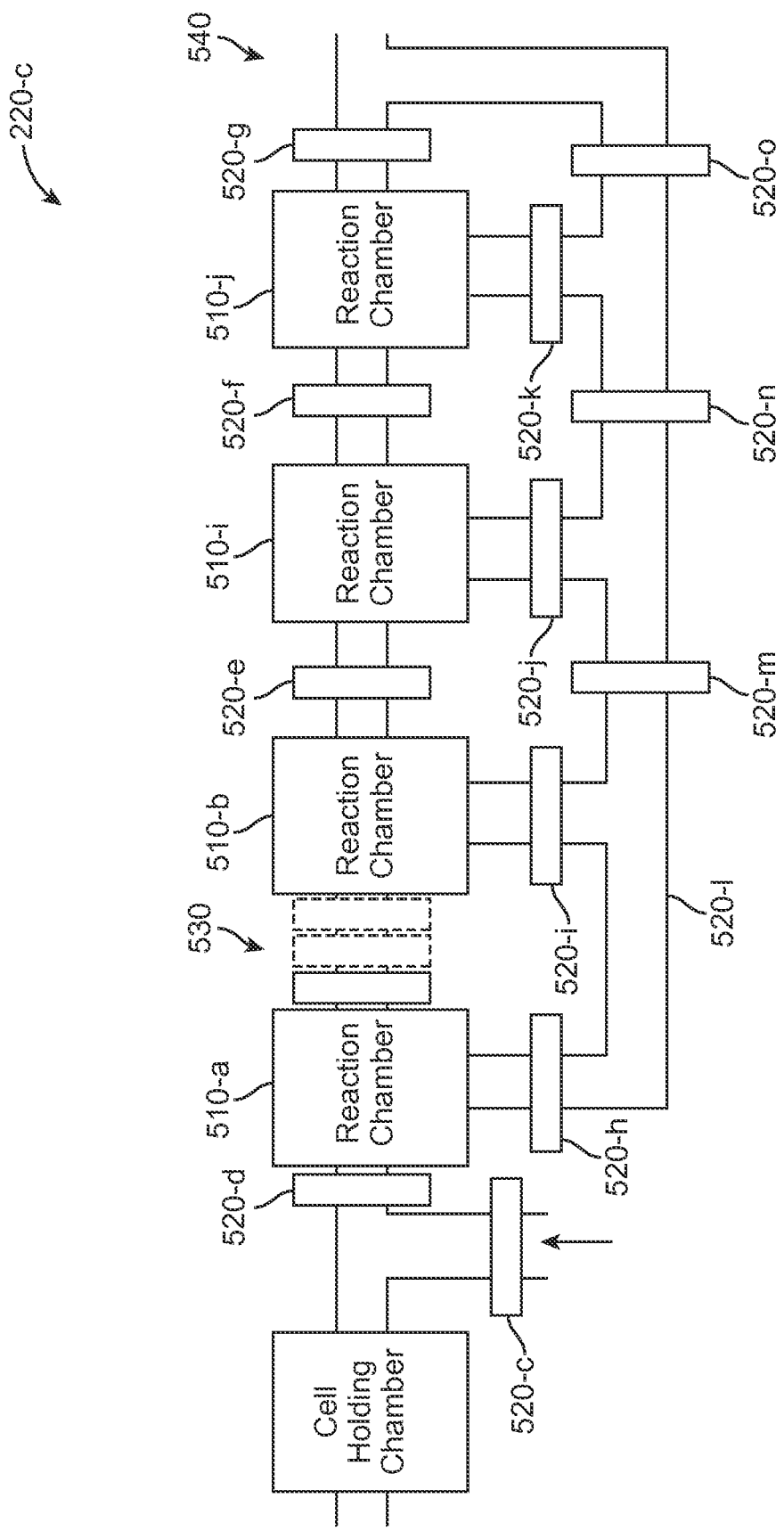
FIG. 8 shows a multi-chamber reaction configuration that may be fluidically connected to the cell holding chamber.

In some embodiments the cell component analysis is carried out in the microfluidic system, such as in a multi-chamber reaction configuration fluidically connected to the cell holding chamber. Analysis includes nucleic acid analysis (e.g., amplification, sequencing or cloning of RNA or DNA from the cell(s)), protein analysis, cell fixation, and any other methods for characterizing a cell or combination of cells. For illustration and not limitation, FIG. 8 shows an example of a multi-chamber reaction configuration 220-c in accordance with various embodiments. Multi-chamber reaction configuration 220-c may include different components or aspects in accordance with various embodiments. Multi-chamber reaction configuration 220-c may be configured to perform different processes including, but not limited to, STA, RT-STA, mRNA-SEQ, preamplification, WMA, multimodal applications, protein applications, sample processor applications, WTA, WGA, real-time PCR preparation, CNV, and/or haplotyping. Multi-chamber reaction configuration 220-c may be configured to perform multiple reaction steps, which may include active mixing.

Multi-chamber reaction configuration 220-c may include numerous valves 520, which may be utilized to control the flow of solutions through multi-chamber reaction configuration 220-c. In some embodiments, a pump 530, such as a peristaltic pump, may be included in multi-chamber reaction configuration 220-c to facilitate transport of solutions through multi-chamber reaction configuration 220-c. Pump 530 may include multiple valves 520; in this example, pump 530 may include three valves. One or more pumps 530 may be located at different locations.

Multi-chamber reaction configuration 220-c may also include multiple reaction chambers 510. In some embodiments, capture configuration 210-c may be considered one of the reaction chambers 510. Merely by way of example, valves 520-d, 520-e, 520-f, and 520-g may be utilized to control the direct flow between reaction chambers 510-a, 510-b, 510-i, and 510-j respective. Additional valves such as valves 520-h-520-o, in different combinations, may be utilized to introduce reagents, mix and/or circulate solutions from one or more reaction chamber 510. Additional valves 520-a and/or 520-b may control flow between different capture configurations. Valve 520-b may be utilized to control flow of solutions such as reagents to capture configuration 210-c. Multi-chamber reaction configuration 220-c may be configured to mix and/or circulate solution during thermal cycling. Reaction products may be delivered 540 to export configuration (not shown) may be referred to as a harvest configuration, harvest well, and/or harvest inlet in some cases.

The multi-chamber reaction configuration is flexible and can be used to isolate and amplify nucleic acids, isolate proteins, make cDNA, and a wide variety of other molecular biological process and assay steps. The system may be also include additional fluidic circuits including, but not limited to, various published or commercially available systems. For example, the Fluidigm BioMark™ HD System can be used for gene expression, single-cell gene expression, single-cell mRNA sequencing, SNP genotyping, copy number variation, sample quantification for sequencing. Fluidigm's qdPCR 37K™ IFC chip may be used for digital PCR. These and other assay systems can be integrated into the system of the invention (i.e., fluidically connected by microfluidic channels) allowing, among other advantages greater automation and shorter processing time. See U.S. Pat. No. 7,604,965; U.S. Pat. Pub. Nos. 2012-0115143 ("Universal Probe Assay Methods"), US 2012-0288857 ("Multifunctional Probe-Primers"), and US 2013-0045881 ("Probe Based Nucleic Acid Detection"); copending commonly owned International Patent Application No. PCT/US2012/065376 ("Nucleic Acid Detection Using Probes"), and copending commonly owned provisional application 61/799,559 ("Simultaneous Detection Of Target Protein And Target Nucleic Acids In A Single Cell"), each of which is expressly incorporated by reference for all purposes.

15. Imaging

In preferred embodiments the system includes an imaging module, integrated into the for imaging one or more cells and locations of the microfluidic device. Methods and equipment for collecting and processing images are known in the art. The imaging module may include at least a microscope or a camera configured to image one or more captured cells in the microfluidic device. In some embodiments the imaging module comprises a CCD camera.

The imaging module may be configured to image one, more than one, or all of the areas of the integrated fluidic circuit, including as partitioning channel(s), cell holding chambers, partitioning channel sectors, holding chamber sectors, post-culture processing sectors, and assay (amplification) sectors.

In some embodiments (e.g., imaging a detectably labeled cell) it is necessary to illuminate the cell(s) and/or reactions at an appropriate wave length, for example in detecting cells labeled with a fluorescent tag or, for example and not limitation, for analysis of an amplification reaction in which a fluorescent signal is generated. Elements such as a filter wheel and other optical elements are known to those of ordinary skill in the art. See, for example, U.S. Pat. No. 7,906,072 incorporated herein by reference.

In one embodiment substantially the entire microfluidic circuit is imaged and optionally displayed to the user. In other embodiments, the partitioning channel is imaged and the cell holding chambers are imaged, without imaging manifolds. In some embodiments software-driven image analysis is used to monitor cells.

The imaging module may be a CCD or CMOS camera that is configured to image the entire microfluidic device without a stitching or scanning process. In one embodiment, the imaging module is further configured to image fluorescence emissions from reactions performed on or within the microfluidic device after cells have been selected and captured. The configuration for selecting the wavelength to be imaged may include fluorescent filters arranged in a filter wheel or a filter cube configuration. In a further embodiment, the filtering of the fluorescent radiation is performed in the imaging module itself, such as within the imaging surface, or by software. The size of the imaged area including cell capture and cell holding sites and reaction sites may be about 30.5×30.5 mm (930.25 mm$^2$) or greater. In another embodiment, the imaged area including cell capture and cell holding sites and reaction sites will be from about 930 to about 1200 mm$^2$ or from about 1200 to 1600 mm$^2$ or from about 1600 to 2000 mm$^2$. In a further embodiment, the imaged area will be from about 2000 to 2600 mm$^2$. The imaging module will generally have an imaging surface, such as a CCD or CMOS imaging surface, which is equivalent to or larger than the imaged area. The imaging surface of the imaging module will typically have from 15,000,000 to 100,000,000 pixels, and sometimes to 200,000,000 pixels, each about 6 to 9 microns in size. In some embodiments, the pixels are about 9 microns in size. A useful range for pixel size is from about 3 to 6 microns or in some embodiments, from about 5 to 7 microns, or from about 6 to 10 microns. In another embodiment, the pixels are about 6 microns in size. The imaging area may further have from about 200,000,000 to about 300,000,000 pixels or from about 300,000,000 to 400,000,000 pixels, In another embodiment, the imaging area will have from about 500,000,000 pixels to about 750,000,000 pixels.

It will be appreciated that in embodiments in which additional assays occur in the system (e.g., real-time PCR assays) the imaging module may be used both for observing the characteristics and movement of cells and for detection of PCR and other reaction products.

16. Automation 16.1 Computer Implementation

It is contemplated that the methods of the invention will be partially automated. For example, based on user input actuation of valves, control pumps, movement of fluid and cells, and imaging can be implemented by computer. It is expected the system will include one or more computer processor modules and/or one or more memory modules that may be used. The computer functions can be integrated into the device or be remote from it.

16.2 User Interface

Figure 9:
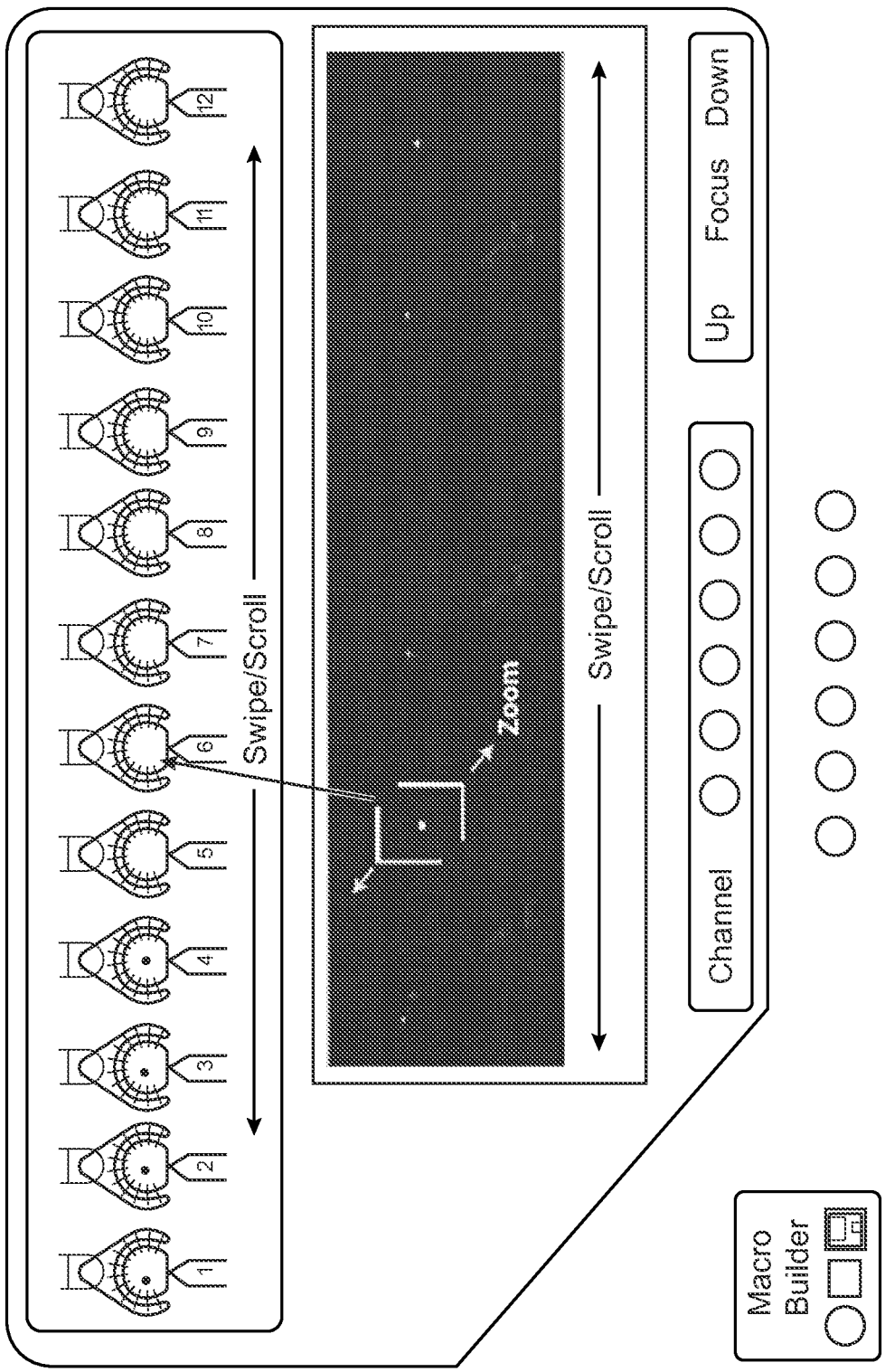
FIG. 9 shows a virtual screen shot of the graphical user interface of the system.

In one aspect the invention provides a user interface to easily carry out automated steps of the method. FIG. 9 provides a virtual screen shot of an exemplary graphical user interface. In general terms, a touchscreen device is provided which shows segments (images or a graphical representation of segments), captured cells in segments (images or a graphical representation of cells, optionally including a representation of cell characteristics) and cell holding chambers (images or a graphical representation of cell holding chambers). Images may be produced using a CCD camera. In one embodiment the touchscreen device shows images of cells and segments, and representations of cell holding chambers. In one embodiment the touchscreen device shows images of cells, and representations of segments and cell holding chambers. The term "representation" is used to encompass both images and graphical representations.

The user, having identified a captured cell or, equivalently, a segment containing a captured cell, of interest instructs the system to transport the cell to a selected cell holding chamber (target). A variety of user gestures can be used. For example, using a drag-and-drop gesture the use taps the image of the cell or segment and drags a finger or cursor to the representation of s specified cell holding chamber. Optionally, an image of the cell moving from the segment to the cell holding chamber is shown. Other gestures may be used. For example, the user may tap on the representation cell (object) at the first location (segment) and then tapping at the destination location (cell holding chamber).

Accordingly, the invention provides a method for transporting cells by manipulating objects in a graphical user interface for a computer, of the type in which representations of objects stored in a memory are displayed to a user on a display, comprising the steps of selecting a first cell whose representation is displayed on said display; dragging the representation of the first cell from a first segment location on the display to a first cell holding chamber; and individually selecting each of a plurality of additional cells and transporting each of them to independently selected cell holding chambers which may the same as or different from the first cell holding chamber Further, the invention provides a graphical user interface for a computer having a display device, comprising a user-controlled component for selecting and moving representations of cells displayed on said display device from a segment on said display device to a cell holding chamber location displayed on said device.

17. Device

Figure 10:
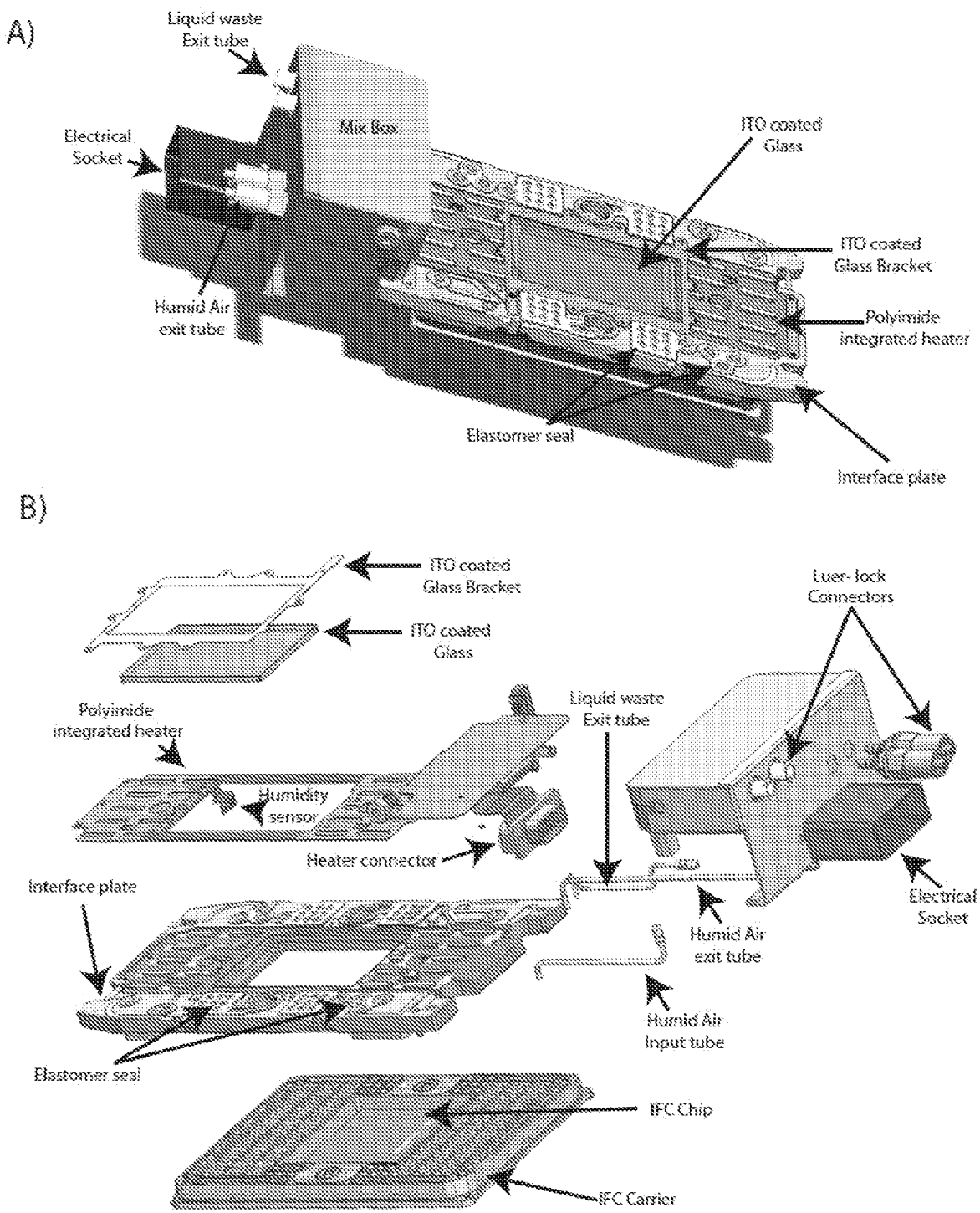
FIG. 10 shows a microfluidic system including an interface plate to enable control of the internal portions the PDMS IFC (e.g., valves and channels) as well as control the environmental conditions surrounding the PDMS chip, e.g., humidity, temperature and gas composition.

An exemplary system of the invention is illustrated in FIG. 10. FIG. 10A shows a top oblique view of the microfluidic chip holding apparatus from the left side. FIG. 10B shows an exploded view of the apparatus from the right side. The holding apparatus is configured to operate the microfluidic device by supplying reagents, maintaining the appropriate temperature and humidity, and operating valves to control the flow of fluid. It comprises a platform at the front side, and a mix box on the back side (shown on the left in FIG. 10A and in the right in FIG. 10B).

Referring to FIG. 10B, the base of the apparatus is an IFC carrier with sample input wells with a cavity shaped and sized to receive a microtiter plate or chip: typically 35 mm square. Above the carrier is an interface plate comprising gaskets connected to control channels in the chip that operate valves by pneumatic control. Above the plate is a layer of polyimide that is configured as an integrated heater to maintain a desired temperature on the platform surrounding the chip, and is connected up to the mix box to bring the input gas mixture up to temperature. Above the heater on the platform is a glass surface surrounded by a glass bracket. The glass is iridium tin coated to inhibit condensation from the moist gasses supplied to the chip. The glass surface is configured to be optically transparent so that each cell in the chip can be located and characterized according to its morphology by imaging. Referring to FIG. 10A, the mix box receives air or a gas mixture appropriate for keeping cells viable in culture (typically 95% O2 and 5% CO2), which is fed from the mix box through the platform to gas supply channels in the chip. The gas mixture is made at least 60%, 80% or 90% humidity to inhibit loss of moisture from the holding chambers of the chip through gas supply channels. After passing through the chip, the humid gas mixture exits from the platform through the mix box and out the humid air exit tube, taking with it any condensation that has formed near the chip.

18. Exemplary Valves, Detectable Labels, Cells, Microfluidic Systems 18.1: Valves Valves of various types are known in the art, including micromechanical valves, elastomeric valves, solid-state microvalves, and others. See, e.g., Felton, 2003, The New Generation of Microvalves" Analytical Chemistry 429-432. Two common approaches to fabrication of microelectromechanical (MEMS) structures such as pumps and valves are silicon-based bulk micro-machining (which is a subtractive fabrication method whereby single crystal silicon is lithographically patterned and then etched to form three-dimensional structures), and surface micro-machining (which is an additive method where layers of semiconductor-type materials such as polysilicon, silicon nitride, silicon dioxide, and various metals are sequentially added and patterned to make three-dimensional structures).

In one embodiment, the valve is a monolithic valve. In a preferred embodiment the valve is a pressure-actuated "elastomeric valve." A pressure-actuated elastomeric valve consists of a configuration in which two microchannels are separated by an elastomeric segment that can be deflected into or retracted from one of the channels (e.g., a flow channel) in response to an actuation force applied to the other channel (e.g., a control channel). Examples of elastomeric valves include upwardly-deflecting valves (see, e.g., US 20050072946), downwardly deflecting valves (see, e.g., U.S. Pat. No. 6,408,878), side actuated valves (see, e.g., US 20020127736, e.g., paragraphs 0215-0219], normally-closed valves (see, e.g., U.S. Pat. Nos. 6,408,878 and 6,899,137) and others. A chemical resistant microfluidic valve with an elastomeric component is described by Hua et al., 2006, J Micromech Microeng 16:1433-1443. In some embodiments a device can have a combination of valves (e.g., upwardly and downwardly deflecting valves). Valves can be actuated by injecting gases (e.g., air, nitrogen, and argon), liquids (e.g., water, silicon oils and other oils), solutions containing salts and/or polymers (including but not limited to polyethylene glycol, glycerol and carbohydrates) and the like into the control channel. Some valves can be actuated by applying a vacuum to the control channel.

In addition to elastomeric valves actuated by pressure-based actuation systems, monolithic valves with an elastomeric component and electrostatic, magnetic, electrolytic and electrokinetic actuation systems may be used. See, e.g., US 20020109114; US 20020127736, e.g., 0168-0176; and U.S. Pat. No. 6,767,706. One-way valves have also been described (see, e.g., Adams et al., 2005, J. Micromech. Microeng.

Other microvalves include microvalve based on electromagnetic actuation (electromagnetic solenoid plungers), piezoelectric effect (disk, cantilever and stack types), pneumatic and thermopneumatic systems, electrostatic actuators, and bimetallic beams (see Shoji et al. 1994, J. Micromech. Microeng. 4(4): 157-171, December 1994), hydrogel-based valves that expand or contract (and thereby close or open) in response to pH changes (Beebe et al. Nature 404(6778): 588-90, 6 Apr. 2000), microfluidic valves comprising electrochemically generated bubbles (Hua et al. Anal Chem. 74(24): 6392-6, 15 Dec. 2002), valves based on polymer monoliths, actuated by UV light (Hasselbrink et al. Anal Chem. 74(19): 4913-8, 1 Oct. 2002), microvalves controlled by electrostatics [U.S. Pat. Nos. 5,417,235 and 5,452,878] or by the thermal buckling of materials (U.S. Pat. No. 5,785, 295).

18.3: Detectable Labels

For monitoring, evaluating, imaging, and otherwise processing a cell by optical means, a suitable detectable label may be, for example and not limitation, colored, fluorescent, luminescent, or phosphorescent. It may be conjugated or bound to the cell surface, or incorporated inside the cell. In some embodiments, it constitutes or is conjugated to an antibody, a lectin, a ligand, a substrate, or a reaction product. Individual cells (or cellular units) may also be tracked and monitored according to a morphological feature that distinguishes them from other cells being processed in the device.

18.4: Cells

The microfluidic devices of this invention typically have channels and chambers that are sized and shaped to permit passage of eukaryotic cells that are both diploid and nucleated. Without implying any limitation on the practice of the invention, such a cell may be derived from a vertebrate, a mammal, a domesticated animal, a mouse, a primate, or a human. It may be an astrocyte, a neuron, a Schwann cell, an epithelial cell, an endothelial cell, an adipocyte, a renal cell, an exocrine cell, a fibroblast, a chondrocyte, an odontocyte, an islet cell, a cardiac cell, a smooth muscle cell, a striated muscle cell, a renal cell, a hepatocyte, a Kuppfer cell, a pituitary cell, a mucous cell, a hormone secreting cell, a keratinocyte, a basal cell, a pneumal cell, a pericyte, or a pulposus cell. It may be a blood related cell such as an erythrocyte, a reticulocyte, a megakaryocyte, a monocyte, a macrophage, a dendritic cell, a granulocyte, an eosinophil, a neutrophil, a basophil, a mast cell, a lymphocyte, a cytotoxic T cell, a helper T cell, a suppressor T cell, a B lymphocyte, a natural killer cell, or a dendritic cell. It may be a cancer or cancer stem cell of various kinds, a leukemia or lymphoma cell, or a hybridoma. It may be a pluripotent or tissue-specific stem cell, a progenitor cell, an oocyte, or a germ cell. Alternatively, it may be a plant cell such as a parenchymal cell, a collenchymal cell, a Sclerenchymal cell, a sclerid cell, a meristematic cell, a xylem cell, or an epidermal cell. Alternatively, it may be a unicellular organism such as a protist or a fungi such as yeast. Cells that are processed or cultured together may be the same type or a plurality of different types in any combination.

Also contemplated is the processing of haploid cells, prokaryotes such as bacteria, anucleated cells such as platelets, and a non-living particles and other entities. In some embodiments, the microfluidic device and its channels are scaled and configured so as to process and allow passage of such cells and particles individually. In other embodiments, the microfluidic device and its channels are scaled and configured so as to process such cells or particles in bulk.

In some embodiments, the cell: is not a gamete, is not an ovum, is not a sperm.

In some embodiments, the combination of cells cultured in a cell holding chamber does not comprise gametes.

In some embodiments, the combination of cells cultured in a cell holding chamber does not comprise both an ovum and a sperm.

18.5: Microfluidic Systems

Devices of the invention can be constructed out of any of various materials or combination of materials from channels, valves and other microfluidic components can be fabricated. Materials from which a chip can be fabricated include, without limitation, elastomers, silicon, glass, metal, polymer, ceramic, inorganic materials, and/or combinations of these materials.

The methods used in fabrication of a microfluidic device will vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" Biotechniques 38:429-46; Beebe et al., 2000, "Microfluidic tectonics: a comprehensive construction platform for microfluidic systems." Proc. Natl. Acad. Sci. USA 97:13488-13493; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, IEEE Trans. on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, MEMS 96, pp. 491496; and Mastrangelo et al., 1989, Vacuum-Sealed Silicon Micromachined Incandescent Ught Source, in Intl. Electron Devices Meeting, IDEM 89, pp. 503-506.

In some embodiments, the device is fabricated using elastomeric materials. Fabrication methods using elastomeric materials will only be briefly described here, because elastomeric materials, methods of fabrication of devices made using such materials, and methods for design of devices and their components have been described in detail (see, e.g., Unger et al., 2000, Science 288:113-16; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application publication Nos. 2004/0115838, 20050072946; 20050000900; 20020127736; 20020109114; 20040115838; 20030138829; 20020164816; 20020127736; and 20020109114; PCT patent publications WO 2005/084191; WO05030822A2; and WO 01/01025; Quake and Scherer, 2000, "From micro to nanofabrication with soft materials" Science 290: 1536-40; Xia et al., 1998, "Soft lithography" Angewandte Chemie-International Edition 37:551-575; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Uu et al., 2003, "Solving the "world-to-chip" interface problem with a microfluidic matrix" Analytical Chemistry 75, 4718-23," Hong et al, 2004, "A nanoliter-scale nucleic acid processor with parallel architecture" Nature Biotechnology 22:435-39; Fiorini and Chiu, 2005, "Disposable microfluidic devices: fabrication, function, and application" Biotechniques 38:429-46; Beebe et al., 2000, "Microfluidic tectonics: a comprehensive construction platform for microfluidic systems." Proc. Natl. Acad. Sci. USA 97:13488-13493; Rolland et al., 2004, "Solvent-resistant photocurable "liquid Teflon" for microfluidic device fabrication" J. Amer. Chem. Soc. 126:2322-2323; Rossier et al., 2002, "Plasma etched polymer microelectrochemical systems" Lab Chip 2:145-150; Becker et al., 2002, "Polymer microfluidic devices" Talanta 56:267-287; Becker et al., 2000, "Polymer microfabrication methods for microfluidic analytical applications" Electrophoresis 21:12-26; Terry et al., 1979, A Gas Chromatography Air Analyzer Fabricated on a Silicon Wafer, IEEE Trans. on Electron Devices, v. ED-26, pp. 1880-1886; Berg et al., 1994, Micro Total Analysis Systems, New York, Kluwer; Webster et al., 1996, Monolithic Capillary Gel Electrophoresis Stage with On-Chip Detector in International Conference On Micro Electromechanical Systems, MEMS 96, pp. 491496; and Mastrangelo et al., 1989, Vacuum-Sealed Silicon Micromachined Incandescent Light Source, in Intl. Electron Devices Meeting, IDEM 89, pp. 503-506; and other references cited herein and found in the scientific and patent literature. In general, the different microfluidic devices described herein may fabricated utilizing a variety of fabrication methods using elastomeric materials, such as PDMS, and methods for design of the microfluidic devices and their components have been described in detail in the scientific and patent literature. See, e.g., Unger et al. (2000) Science 288:113-116; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Micro fluidic devices including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 200210164816; 2002/0127736; and 2002/0109114; PCT Publication Nos. WO 2005/084191; WO 05/030822A2; and WO 01101025; Quake and Scherer, 2000, "From micro to nanofabrication with soft materials" Science 290: 1536-40; Unger et at., 2000, "Monolithic microfabricated valves and pumps by multilayer soft lithography" Science 288: 113-116; Thorsen et at., 2002, "Micro fluidic large-scale integration" Science 298:580-584; Chou et at., 2000, "Microfabricated Rotary Pump" Biomedical Microdevices 3:323-330; Liu et at., 2003, "Solving the "world-to-chip" interface problem with a microfluidic matrix" Analytical Chemistry 75, 4718-23, Hong et. al, 2004, "A nanoliter-scale nucleic acid processor with parallel architecture" Nature Biotechnology 22:435-39, all incorporated by reference for all purposes.

Certain characteristics of microfluidic channels will vary with their function. For example, channels through which cells are transported will have dimensions suitable for the types of cells being studied. Channels though which solutions (e.g., cell media) are transported typically have smaller dimensions. Control channels, which are used in certain elastomeric microfluidic devices to actuate valves, may have dimensions that vary. Thus the dimensions of channels can vary widely but typically include at least one cross-sectional dimension (e.g., height, width, or diameter) less than 2 mm, generally less than 1 mm, sometimes less than 0.5 mm, and sometimes less than 0.3 mm. Channels often have at least one cross-sectional dimension in the range of 0.05 to 1000 microns, sometimes 0.2 to 500 microns, and sometimes 10 to 250 microns. The channel may have any suitable cross-sectional shape that allows for fluid and/or cell transport, for example, a square channel, a circular channel, a rounded channel, a rectangular channel, etc. In an exemplary aspect, flow channels are rectangular and have widths of about in the range of 0.05 to 1000 microns, sometimes 0.2 to 500 microns, and sometimes 10 to 250 microns. In an exemplary aspect, channels have depths of 0.01 to 1000 microns, sometimes 0.05 to 500 microns, sometimes 0.2 to 250 microns, and sometimes 1 to 100 microns. In an exemplary aspect, flow channels have width-to-depth ratios of about 0.1:1 to 100:1, more preferably 1:1 to 50:1, more preferably 2:1 to 20:1, and most preferably 3:1 to 15:1, and often about 10:1.

Microfluidic devices of the present invention may include one or more integral pumps for transport of fluids through flow channels and into and out of other device components (e.g., column or reactors) or the device itself. Suitable pumps can be electronic, electrostatic, magnetic, mechanical, syringe, pneumatic, or peristaltic. Preferably peristaltic pumps, such as those described in U.S. Pat. No. 6,408,878 are used. Alternatively pumps can be external to the chip. Pumps are also used to transport fluids (e.g., water) through control channels to actuate valves. Pumps are also used to draw a vacuum in, for example, vent channels.

Other microfluidic components also can be integrated into the chip, including, for example, control channels, guard channels, vent channels, fluid reservoirs, mixing reactors, rotary mixers, separation modules (e.g., separation columns), sorting regions, pumps, ports, vias, nozzles, monitoring systems, lenses, sensors, temperature control systems, heat sources, light sources, waveguides and the like.

It is understood that the examples and embodiments described herein are for illustrative purposes only and that various modifications or changes in light thereof will be suggested to persons skilled in the art and are to be included within the spirit and purview of this application and scope of the appended claims. In addition, all other publications, patents, and patent applications cited herein are hereby incorporated by reference in their entirety for all purposes.

We claim:

1. A method for cell analysis in a microfluidic device comprising a plurality of cell holding chambers, said method comprising carrying out at least two rounds of cell capturing, characterization, and transport, each round comprising:
   a) flowing a solution comprising a plurality of individual cells into a first microfluidic channel; then
   b) actively partitioning the first microfluidic channel into a plurality of contiguous segments, thereby capturing at least one cell in at least one segment, wherein one or more of said segments comprises a single captured cell;
   c) determining at least one characteristic of one or more of said single captured cells;
   d) selecting one or more of the single captured cells in (c) based on the determined characteristic(s); and
   e) independently transporting each said single captured cell selected in (d) to a specified cell holding chamber, whereby for each specified cell holding chamber the characteristic(s) of cell(s) transported thereto is known, wherein said transporting comprises directing flow out from one of the segments containing a single captured cell to transport said single cell from said segment to a connecting channel and into the specified cell holding chamber.

2. The method of claim 1 wherein in step (b) comprises partitioning the channel into at least 5 segments and the majority of said segments comprise no more than one cell.

3. The method of claim 1 wherein the number of individual cells flowed into the portion of the first microfluidic channel that is partitioned is less than the number of segments produced as a result of the partitioning.

4. The method of claim 1 wherein the device comprises two or more first microfluidic channels and wherein a cell is transported from any segment of any first microfluidic channel to any cell holding chamber.

5. The method of claim 1 wherein the characteristic determined is cell size, morphology, or the presence or absence of an extracellular or intracellular antigen.

6. The method of claim 1 wherein the characteristic determined is the response by the cell to a physical, chemical or biological challenge.

7. The method of claim 1 comprising transporting said cells by bulk fluid flow.

8. The method of claim 1 comprising independently transporting individual cells from segments to a single connector channel, and then through a distributing manifold to said specified cell holding chambers.

9. The method of claim 1 comprising transporting captured cells through a common second microfluidic channel in fluidic communication with said segments in transit to a specified cell holding chamber.

10. The method of claim 1 wherein the ratio of the number of segments to the number of cell holding chambers is greater than 1.

11. The method of claim 1 comprising individually capturing multiple cells and individually transporting two or more of said individually captured multiple cells to the same cell holding chamber, thereby producing a cell holding chamber comprising a defined combination of cells.

12. The method of claim 1 comprising culturing the cells in the cell holding chamber.

13. The method of claim 12 comprising culturing the cells for from about 1 hour to about 24 hours, wherein the cells are challenged during culturing, and wherein the challenge comprises exposing the cells to an agent selected from a drug, test agent, protein, nucleic acid or small molecule.

14. The method of claim 12 comprising, after a period of culture, harvesting viable cells from a cell holding chamber.

15. The method of claim 1, further comprising the step of treating a cell located in a first cell holding chamber with a reagent, solution or physical stimulus, and said treating results in lysis of said cell and release of macromolecules from said cell.

16. The method of claim 15 comprising transporting macromolecules released from the lysed cell from the first cell holding chamber to a corresponding microfluidic reaction chamber.

17. The method of claim 16 wherein the macromolecules are nucleic acids, and the method comprises amplifying the nucleic acids.

18. The method of claim 1 comprising flowing the cells in the first microfluidic channel that are not selected into a waste reservoir.

* * * * *